US010180505B2

(12) United States Patent
Censor et al.

(10) Patent No.: US 10,180,505 B2
(45) Date of Patent: Jan. 15, 2019

(54) SYSTEMS AND METHODOLOGIES FOR PROTON COMPUTED TOMOGRAPHY

(71) Applicants: University of Haifa, Haifa (IL); University of Wollongong, Wollongong NSW (AU); Loma Linda University Medical Center, Loma Linda, CA (US)

(72) Inventors: Yair Censor, Haifa (IL); Scott N. Penfold, North Adelaide (AU); Reinhard W. Schulte, Grand Terrace, CA (US)

(73) Assignees: LOMA LINDA UNIVERSITY MEDICAL CENTER, Loma Linda, CA (US); UNIVERSITY OF HAIFA, Haifa (IL); UNIVERSITY OF WOLLONGONG, Wollongong (AU)

( * ) Notice: Subject to any disclaimer, the term of this patent is extended or adjusted under 35 U.S.C. 154(b) by 250 days.

(21) Appl. No.: 14/799,910

(22) Filed: Jul. 15, 2015

(65) Prior Publication Data
US 2016/0077223 A1 Mar. 17, 2016

Related U.S. Application Data

(63) Continuation of application No. 13/026,051, filed on Feb. 11, 2011, now Pat. No. 9,207,193.

(60) Provisional application No. 61/303,783, filed on Feb. 12, 2010.

(51) Int. Cl.
| *G01N 33/48* | (2006.01) |
| *G01N 33/50* | (2006.01) |
| *G01T 1/29* | (2006.01) |
| *G06F 19/12* | (2011.01) |
| *G06F 19/24* | (2011.01) |
| *G01N 23/046* | (2018.01) |
| *A61N 5/10* | (2006.01) |
| *A61B 6/03* | (2006.01) |
| *A61B 6/00* | (2006.01) |
| *G06T 11/00* | (2006.01) |
| *G01T 1/17* | (2006.01) |

(52) U.S. Cl.
CPC ............ *G01T 1/2985* (2013.01); *A61B 6/032* (2013.01); *A61B 6/4241* (2013.01); *A61B 6/4258* (2013.01); *A61B 6/4266* (2013.01); *A61B 6/5205* (2013.01); *A61B 6/583* (2013.01); *A61N 5/10* (2013.01); *G01N 23/046* (2013.01); *G01T 1/17* (2013.01); *G06F 19/12* (2013.01); *G06F 19/24* (2013.01); *G06T 11/006* (2013.01); *A61N 2005/1087* (2013.01); *G01N 2223/419* (2013.01)

(58) Field of Classification Search
None
See application file for complete search history.

(56) References Cited

U.S. PATENT DOCUMENTS

| 2,629,831 A | 2/1953 | Atchley, Jr. |
| 3,604,931 A | 9/1971 | Kastner et al. |
| 3,621,240 A | 11/1971 | Cohen et al. |
| 3,901,588 A | 8/1975 | Longhenry |
| 3,942,012 A | 3/1976 | Boux |
| 3,955,089 A | 5/1976 | McIntyre et al. |
| 3,975,640 A | 8/1976 | Boux et al. |
| 3,986,026 A | 10/1976 | Martin |
| 4,020,356 A | 4/1977 | Brahme |
| 4,069,457 A | 1/1978 | Martin et al. |
| 4,070,611 A | 1/1978 | Ernst |
| 4,095,114 A | 6/1978 | Taumann |
| 4,112,306 A | 9/1978 | Nunan |
| 4,118,631 A | 10/1978 | Froggatt |
| 4,190,772 A | 2/1980 | Dinwiddie et al. |
| 4,206,355 A | 6/1980 | Boux |
| 4,287,425 A | 9/1981 | Elliott, Jr. |
| 4,602,622 A | 7/1986 | Bar et al. |
| 4,691,332 A | 9/1987 | Burstein |
| 4,726,046 A | 2/1988 | Nunan |
| 4,870,287 A | 9/1989 | Cole et al. |
| 5,107,839 A | 4/1992 | Houdek et al. |
| 5,115,391 A | 5/1992 | Puthenpura et al. |

(Continued)

FOREIGN PATENT DOCUMENTS

| DE | 10 2007 032 025 | 12/2008 |
| JP | 03-094736 A | 4/1991 |

(Continued)

OTHER PUBLICATIONS

Aharoni et al.: "Block-Iterative Projection Methods for Parallel Computation of Solutions to Convex Feasibility Problems," Linear Algebra and its Applications 120:165-175 (1989).

(Continued)

*Primary Examiner* — Russell S Negin
(74) *Attorney, Agent, or Firm* — Knobbe, Martens, Olson & Bear, LLP

(57) ABSTRACT

Disclosed are systems, devices and methodologies relating to proton computed tomography. In some implementations, detection of protons can yield track information before and after an object for each proton so as to allow determination of a likely path of each proton within the object. Further, measurement of energy loss experienced by each proton allows determination that a given likely path results in a given energy loss. A collection of such data allows characterization of the object. In the context of energy loss, such a characterization can include an image map of relative stopping power of the object. Various reconstruction methodologies for obtaining such an image, including but not limited to superiorization of a merit function such as total variation, are disclosed. In some implementations, various forms of total variation superiorization methodology can yield excellent results while being computationally efficient and with reduced computing time. In some implementations, such a methodology can result in high quality proton CT images using relatively low dose of protons.

20 Claims, 24 Drawing Sheets

(56) References Cited

U.S. PATENT DOCUMENTS

| | | | |
|---|---|---|---|
| 5,117,829 A | 6/1992 | Miller et al. |
| 5,206,893 A | 4/1993 | Hara |
| 5,402,463 A | 3/1995 | Umetani et al. |
| 5,446,548 A | 8/1995 | Gerig et al. |
| 5,511,549 A | 4/1996 | Legg et al. |
| 5,538,494 A | 7/1996 | Matsuda |
| 5,553,112 A | 9/1996 | Hardy et al. |
| 5,585,642 A | 12/1996 | Britton et al. |
| 5,596,199 A | 1/1997 | McNulty et al. |
| 5,596,619 A | 1/1997 | Carol |
| 5,602,892 A | 2/1997 | Llacer |
| 5,612,783 A | 3/1997 | Hirsh |
| 5,622,170 A | 4/1997 | Schultz |
| 5,777,325 A | 7/1998 | Weinberger et al. |
| 5,825,845 A | 10/1998 | Blair et al. |
| 5,851,182 A | 12/1998 | Sahadevan |
| 5,963,658 A | 10/1999 | Klibanov et al. |
| 5,981,946 A | 11/1999 | Mason |
| 6,052,435 A | 4/2000 | Hernandez-Guerra et al. |
| 6,104,779 A | 8/2000 | Shepherd et al. |
| 6,148,272 A | 11/2000 | Bergstrom et al. |
| 6,178,389 B1 | 1/2001 | Sola et al. |
| 6,195,409 B1 | 2/2001 | Chang et al. |
| 6,200,025 B1 | 3/2001 | Rich |
| 6,256,591 B1 | 7/2001 | Yoda et al. |
| 6,307,914 B1 | 10/2001 | Kuneida et al. |
| 6,316,776 B1 | 11/2001 | Hiramoto et al. |
| 6,345,114 B1 | 2/2002 | Mackie et al. |
| 6,385,286 B1 | 5/2002 | Fitchard et al. |
| 6,420,711 B2 | 7/2002 | Tümer |
| 6,445,766 B1 | 9/2002 | Whitham |
| 6,466,813 B1 | 10/2002 | Shukla et al. |
| 6,473,490 B1 | 10/2002 | Siochi |
| 6,477,223 B1 | 11/2002 | Francke |
| 6,490,477 B1 | 12/2002 | Zlka et al. |
| 6,504,899 B2 | 1/2003 | Pugachev et al. |
| 6,560,354 B1 | 5/2003 | Maurer, Jr. et al. |
| 6,565,577 B2 | 5/2003 | Cosman |
| 6,628,745 B1 | 9/2003 | Annis et al. |
| 6,694,057 B1 | 2/2004 | Miller et al. |
| 6,731,970 B2 | 5/2004 | Schlossbauer et al. |
| 6,754,299 B2 | 6/2004 | Patch |
| 6,757,355 B1 | 6/2004 | Siochi |
| 6,787,771 B2 | 9/2004 | Bashkirov et al. |
| 6,799,068 B1 | 9/2004 | Hartmann et al. |
| 6,804,548 B2 | 10/2004 | Takahashi et al. |
| 6,810,107 B2 | 10/2004 | Steinberg |
| 6,814,694 B1 | 11/2004 | Pedroni |
| 6,906,317 B2 | 6/2005 | Bateman et al. |
| 6,953,943 B2 | 10/2005 | Yanagisawa et al. |
| 6,977,987 B2 | 12/2005 | Yamashita et al. |
| 6,983,034 B2 | 1/2006 | Wang et al. |
| 7,081,619 B2 | 7/2006 | Bashkirov et al. |
| 7,085,347 B2 | 8/2006 | Mihara et al. |
| 7,142,634 B2 | 11/2006 | Engler et al. |
| 7,177,390 B2 | 2/2007 | Martin et al. |
| 7,193,227 B2 | 3/2007 | Hiramoto et al. |
| 7,207,715 B2 | 4/2007 | Yue |
| 7,247,869 B2 | 7/2007 | Tadokoro et al. |
| 7,268,358 B2 | 9/2007 | Ma et al. |
| 7,398,309 B2 | 7/2008 | Baumann et al. |
| 7,629,598 B2 | 12/2009 | Harada |
| 7,801,270 B2 | 9/2010 | Nord et al. |
| 7,820,989 B2 | 10/2010 | Sommer |
| 7,860,216 B2 | 12/2010 | Jongen et al. |
| 8,045,679 B2 | 10/2011 | Balakin |
| 8,080,801 B2 | 12/2011 | Safai |
| 8,109,865 B2 | 2/2012 | Jackson |
| 8,129,699 B2 | 3/2012 | Balakin |
| 8,189,889 B2 | 5/2012 | Pearlstein et al. |
| 8,264,174 B2 | 9/2012 | Liu et al. |
| 8,405,050 B2 | 3/2013 | Bert et al. |
| 8,426,824 B2 | 4/2013 | Jongen et al. |
| 8,632,448 B1 | 1/2014 | Schulte et al. |
| 8,737,707 B2 | 5/2014 | Pearlstein et al. |
| 8,750,453 B2 | 6/2014 | Cheng et al. |
| 8,841,602 B2 | 9/2014 | Schulte et al. |
| 9,084,887 B2 | 7/2015 | Schulte et al. |
| 9,196,082 B2 | 11/2015 | Pearlstein et al. |
| 9,207,193 B2 * | 12/2015 | Censor |
| 9,220,920 B2 | 12/2015 | Schulte et al. |
| 9,880,301 B2 | 1/2018 | Schulte et al. |
| 2001/0016029 A1 | 8/2001 | Tumer |
| 2002/0065461 A1 | 5/2002 | Cosman |
| 2002/0077545 A1 | 6/2002 | Takahashi et al. |
| 2002/0193685 A1 | 12/2002 | Mate et al. |
| 2003/0007601 A1 | 1/2003 | Jaffray et al. |
| 2003/0095625 A1 | 5/2003 | Steinberg |
| 2003/0122544 A1 | 7/2003 | Parker et al. |
| 2003/0155530 A1 | 8/2003 | Adnani et al. |
| 2004/0034438 A1 | 2/2004 | Uematsu |
| 2004/0042583 A1 | 3/2004 | Wackerle et al. |
| 2004/0158145 A1 | 8/2004 | Ghelmansarai et al. |
| 2005/0078787 A1 | 4/2005 | Dinten et al. |
| 2005/0152502 A1 | 7/2005 | Saunders et al. |
| 2006/0104410 A1 | 5/2006 | Sauer et al. |
| 2006/0166353 A1 | 7/2006 | Alfano et al. |
| 2006/0175529 A1 | 8/2006 | Harmon et al. |
| 2007/0031337 A1 | 2/2007 | Schulte |
| 2007/0086560 A1 | 4/2007 | Kia et al. |
| 2007/0122020 A1 | 5/2007 | Claus et al. |
| 2007/0147672 A1 | 6/2007 | Karl et al. |
| 2007/0181815 A1 | 8/2007 | Ebstein |
| 2008/0031414 A1 | 2/2008 | Coppens |
| 2008/0071131 A1 | 3/2008 | Rietzel |
| 2008/0083871 A1 | 4/2008 | Cravens et al. |
| 2008/0228418 A1 | 9/2008 | Green |
| 2009/0274269 A1 | 5/2009 | Foland |
| 2009/0168960 A1 | 7/2009 | Jongen et al. |
| 2009/0196393 A1 | 8/2009 | Wang et al. |
| 2009/0230315 A1 | 9/2009 | Hunter et al. |
| 2010/0032564 A1 | 2/2010 | Morris et al. |
| 2010/0301235 A1 | 12/2010 | Bert et al. |
| 2011/0006224 A1 | 1/2011 | Maltz et al. |
| 2011/0118531 A1 | 5/2011 | Balakin |
| 2011/0196223 A1 | 8/2011 | Balakin |
| 2011/0220794 A1 | 9/2011 | Censor et al. |
| 2011/0309255 A1 | 12/2011 | Bert et al. |
| 2012/0056109 A1 | 3/2012 | Lomax |
| 2012/0104270 A1 | 5/2012 | Marchand et al. |
| 2012/0136194 A1 | 5/2012 | Zhang et al. |
| 2012/0165651 A1 | 6/2012 | Inaniwa et al. |
| 2012/0205557 A1 | 8/2012 | Rinecker |
| 2012/0271164 A1 | 10/2012 | Gagnon |
| 2013/0015352 A1 | 1/2013 | Karonis et al. |
| 2013/0251229 A1 | 9/2013 | Ramirez Giraldo et al. |
| 2014/0350322 A1 | 11/2014 | Schulte |
| 2016/0016010 A1 | 1/2016 | Schulte |

FOREIGN PATENT DOCUMENTS

| | | |
|---|---|---|
| JP | 2008-113792 A | 5/2008 |
| WO | WO 87/000682 | 1/1987 |
| WO | WO 98/018523 | 5/1998 |
| WO | WO 03/020196 | 3/2003 |
| WO | WO 07/095312 | 8/2007 |
| WO | WO 07/126782 | 11/2007 |
| WO | WO 08/067842 | 6/2008 |
| WO | WO 08/140560 | 11/2008 |
| WO | WO 09/135202 | 11/2009 |
| WO | WO 09/142548 | 11/2009 |
| WO | WO 10/011676 | 1/2010 |
| WO | WO 10/109586 | 9/2010 |
| WO | WO 10/149740 | 12/2010 |
| WO | WO 11/100628 | 8/2011 |
| WO | WO 11/154853 | 12/2011 |
| WO | WO 11/162851 | 12/2011 |
| WO | WO 12/024448 | 2/2012 |
| WO | WO 12/161852 | 11/2012 |

(56) References Cited

FOREIGN PATENT DOCUMENTS

| WO | WO 2015/195570 | 3/2016 |
|----|----------------|--------|
| WO | WO 2017/053869 | 3/2017 |

OTHER PUBLICATIONS

Andersen et al.: "Simultaneous Algebraic Reconstruction Technique (SART): A Superior Implementation of the Art Algorithm," Ultrasonic Imaging 6, 81-94 (1984).
Archambeau et al.: "Conceptual Design of a Proton Therapy Synchrotron for Loma Linda University Medical Center," Fermi National Accelerator Laboratory, Jun. 1986, in 106 pages.
Archambeau et al.: "Design of a Proton Therapy Synchrotron," Fermi National Accelerator Laboratory, Jun. 1986, pp. LL467-LL574 in 54 pages.
Bashkirov et al.: "Development of Proton Computed Tomography for Applications in Proton Therapy," CP1099, Application of Accelerators in Research and Industry. 20th International Conference 2009 American Institute of Physics.
Bruzzi et al.: "Prototype Tracking Studies for Proton CT," IEEE Transactions on Nuclear Science, vol. 54, No. 1, Feb. 2007.
Butnariu, D. et al.: "Stable Convergence Behavior Under Summable perturbations of a Class of Projection Methods for Convex Feasibility and Optimization Problems," IEEE Journal of Selected Topics in Signal Processing, vol. 1. No. 4, Dec. 2007.
Butnariu, D. et al.: "Stable Convergence Theorems for Infinite Products and Powers of Nonexpansive Mappings," Numerical Functional Analysis and Optimization, vol. 29, pp. 304-323, 2008.
Censor, Y. et al.: "Averaging Strings of Sequential Iterations for Convex Feasibility Problems," Inherently Parallel Algorithms in Feasibility and Optimization and their Applications 2001 Elsevier Science B.V.
Censor, Y. et al.: "Component averaging: An efficient iterative parallel algorithm for large and sparse unstructured problems," Parallel Computing 27 (2001) 777-808.
Censor, Y. et al.: "On Diagonally-Relaxed Orthogonal Projection Methods," SIAM Journal on Scientific Computing, vol. 30, pp. 473-504, (2008).
Censor, Y. et al.: "Perturbation Resillience and Superiorization of Iterative Algorithms," Inverse Problems, vol. 26, Issue6, p. 065008, May 21, 2010.
Chi-square test, 1995, 3 pages. In Dictionary of Economics, Wiley. Retrieved online on Nov. 28, 2012 from «http://www.credoreference.com/entry/ wileyecon/chi_square_test».
Cole et al.: "Proceedings of a Medical Workshop on Accelerators for Charged-Particle Beam Therapy," by Fermilab, Jan. 24-25, 1985, LL33170-LL33313 in 144 pages.
Combettes, P.L., et al.: "An Adaptive Level Set Method for Nondifferentiable Constrained Image Recovery," IEEE Transactions on Image Processing, vol. 11, No. 11, Nov. 2002.
Combettes, P.L., On the Numerical Robustness of the Parallel Projection Method in Signal Synthesis, IEEE Signal Processing Letters, vol. 8 pp. 45-47, Feb. 2001.
Davidi, R., et al., Perturbation-resilient Block-iterative Projection Methods with Application to Image Reconstruction from Projections, International Transactions in Operational Research, vol. 16, pp. 505-524, 2009.
Davidi, Ran, Algorithms for Superiorization and their Applications to Image Reconstruction, Department of Computer Science, The City University of New York, NY, USA, in 123 pages, 2010.
Dicello et al.: "Microdosimetric Comparison of Scanned and Conventional Proton Beams Used in Radiation Therapy," Radiation Protection Dosimetry (2011), vol. 143, No. 204, pp. 513-518.
Feldt et al.: "Prototype Tracking Studies for Proton CT," 2005 IEEE Nuclear Science Symposium Conference Record, N302.
Garduño, E., et al.: "Reconstruction From a Few Projections by $\ell$ 1-minimization of the Haar Transform," Inverse Problems, vol. 27, 055006, Apr. 7, 2011.
Herman: "Algebraic Reconstruction Techniques," Fundamentals of Computerized Tomography, Image Reconstruction from Projections, Second Edition, Springer-Verlag London Limited 2009. Chapter 11, pp. 193-216.
Herman: "Backprojection," Fundamentals of Computerized Tomography, Image Reconstruction from Projections, Second Edition, Springer-Verlag London Limited 2009. Chapter 7, pp. 125-133.
Herman: "Basic Concepts of Reconstruction Algorithms," Fundamentals of Computerized Tomography, Image Reconstruction from Projections, Second Edition, Springer-Verlag London Limited 2009. Chapter 6, pp. 101-124.
Herman: "Quadratic Optimization Methods," Fundamentals of Computerized Tomography, Image Reconstruction from Projections, Second Edition, Springer-Verlag London Limited 2009. Chapter 12, pp. 217-233.
Herman, G.T. et al., "Image Reconstruction From a Small Number of Projections," Inverse Problems, vol. 24, 045011 (17pp), Jun. 19, 2008.
Hurly et al.: "Callibration of a Prototype Proton CT Scanner," Med. Phys. 38, 3568 (2011).
Hurley et al.: "Water-equivalent path length calibration of a prototype proton CT scanner," Medical Physics 39, 2438 (2012).
International Search Report and Written Opinion of the International Search Authority in PCT/US2011/024644 (WO 2011/100628), dated Aug. 9, 2011.
International Search Report and Written Opinion, dated Nov. 28, 2012, re PCT/US2012/027911.
Krause et al.: "Adaption of a Synchrotron Control System for Heavy Ion Tumor Therapy," Proceedings of the 1995 International Conference on Accelerator and Large Experimental Physics Control Systems (ICALEPCS1995), Chicago, IL, Oct. 30-Nov. 3, 1995, McC. Crowley-Milling (ed.), P. Lucas (ed.), P. Schoessow (ed.)., Fermi Lab-Co NF-96-069, 1996 S. 14-19.
Lalush et al.: "Improving the convergence of iterative filtered backprojection algorithms," Medical Physics, vol. 21, 1994, pp. 1283-1286.
Le et al.: "Intelligent ePR system for evidence-based research in radiotherapy: proton therapy for prostate cancer," Int J CARS (2011) 6:769-784.
Li et al.: "Reconstruction with most likely trajectory for proton computed tomography." Medical Imaging 2004. Proceedings of SPIE vol. 5370.
Li et al.: "Reconstruction for proton computed tomography by tracing proton trajectories: A Monte Carlo study," Medical Physics, vol. 33, 2006, pp. 699-706.
Li et al : "Sparse Object Reconstruction From a Limited Number of Projections Using the Linear Programming," Nuclear Science Symposium Conference Record, 2002 IEEE, Nov. 16, 2002, vol. 2, pp. 989-993.
Litt et al.: "Application of Nonlinear system identification to magnetic resonance imaging and computed tomography," 1995 IEEE-EMBC and CMBRC, Theme 6: Physiological Systems/ Modelling and Identification. pp. 1389-1390.
McAllister et al.: "General Purpose Graphics Processing Unit Speedup of Integral Relative Electron Density Calculation for Proton Computed Tomography," 2009 IEEE Nuclear Science Symposium Conference Record, HP3-2.
Mueller et al.: "Reconstruction for proton computed tomography: A practical approach," presented at the 2003 IEEE Nuclear Science Symposium and Medical Imaging Conference, paper M14-342.
Pemler et al.. "A detector system for proton radiography on the gantry of the Paul-Scherrer-Institute," Nucl. Instrum, Meth. A, vol. 432, No. 2-3, pp. 483-495, 1999.
Penfold et al.: "Block-Iterative and String-Averaging Projection Algorithms in Proton Computed Tomography Image Reconstruction," Biomedical Mathematics: Promising Directions in Imaging, Therapy Planning, and Inverse Problems. The Huangguoshu International Interdisciplinary Conference on Biomedical Mathematics, The Huanggoushu National Park of China, Guizhou, China—Nov. 3-9, 2008.
Penfold et al.: "Total variation superiorization schemes in proton computed tomography image reconstruction," Med. Phys. 37 (11), Nov. 2010.

(56) References Cited

OTHER PUBLICATIONS

Penfold et al.: "A more accurate reconstruction system of matrix for quantitative proton computed tomography," Med. Phys 36 (10), Oct. 2009, pp. 4511-4518.
Penfold et al.: "Characteristics of Proton CT Images Reconstruction with Filtered Backprojection and Iterative Projection Algorithms," Nuclear Science Symposium Conference Record (NSS/MIC), 2009 IEEE, Nov. 1, 2009, pp. 4176-4180.
Penfold et al.: "Geometrical optimization of a particle tracking system for proton computed tomography," Radiation Measurements 46 (2011) 2069-2071.
Penfold: "Image Reconstruction and Monte Carlo Simulations in the Development of Proton Computed Tomography for Applications in Proton Radiation Therapy," Doctor of Philosophy dissertation, Centre for Medical Radiation Physics, University of Wollongong, 2010. Retrieved from the Internet http://ro.uow.edu.au/theses/3305; in 202 pages.
Petterson et al.: "Proton Radiography Studies for Proton CT," IEEE Nuc. Sci. Symp. Conf. 2006.
"Product Overview," by BrainLAB Radiotherapy Solutions, 2004, BrainLAB AG, in 6 pages.
Proton Therapy Facility: Engineering Design Report, by Fermi National Accelerator Laboratory, Feb. 1987, LL45441-LL45570, in 130 pages.
Sadrozinski et al.: "Issues in Proton Computed Tomography," Nuclear Instruments and Methods in Physics Research A 511, Jun. 2003, pp. 275-281, in 7 pages.
Sadrozinski et al.: "Development of a head scanner for proton CT," Nuclear Instruments and Methods in Physics Research A 699 (2013) 205-210.
Schulte et al.: "A maximum likelihood proton path formalism for application in proton computed tomography," Medical Physics 35, 4849 (2008).
Schulte et al.: "Design of a Proton Computed Tomography System for Applications in Proton Radiation Therapy," Nuclear Science Symposium Conference Record, 2003 IEEE, Oct. 25, 2003, vol. 3, pp. 1579-1583.
Schulte et al.: "Conceptual Design of a Proton Computed Tomography System for Applications in Proton Radiation Therapy," IEEE Transactions on Nuclear Science, Jun. 2004, pp. 866-872, vol. 51(3), in 7 pages.
Schulte et al.: "Nanoparticle-Enhanced Proton Computed Tomography: A Monte Carlo Simulation Study," Biomedical Imaging: Nano to Macro, 2004, IEEE International Symposium, Apr. 15-18, 2004, pp. 1354-1356 in 3 pages.
Schulte et al.: "Density resolution of proton computed tomography," Med Phys. 32 (4), Apr. 2005.
Schulte et al.: "Proton CT for Improved Stopping Power Determination in Proton Therapy, invited," Trans Am Nucl Soc. 2012; 106: 55-58.
Schulte et al.: "Proton Computed Tomography Imaging for Proton Radiation Therapy," Scientific Formal (Paper) Presentations, presented on Dec. 1, 2011. (Abstract Archives of the RSNA, 2011), Abstract Only.
Sidky, E.Y., et al., Image Reconstruction in Circular Cone-Beam Computed Tomography by Constrained, Total-variation Minimization, Physics in Medicine and Biology, vol. 53, (17), 4777-4807, Aug. 13, 2008.
Steckner et al.: "Computing the modulation transfer function of a magnetic resonance imager," Medical Physics, 1994, vol. 21, pp. 483-489.
Takada et al.: "Proton computed tomography with a 250 MeV pulsed beam," Nucl. Instrum. Meth. A, vol. 273, No. 1, pp. 410-422, 1988.
Wong et al.: "The Effect of Tissue Inhomogeneities on the Accuracy of Proton Path Reconstruction for Proton Computed Tomography," CP1099, Application of Accelerators in Research and Industry: 20th International Conference 2009 American Institute of Physics.
Xu et al.: "Towards a unified framework for rapid 3D computed tomography on Commodity GPUs," Manuscript received Oct. 29, 2003. IEEE, 2004, pp. 2757-2759.
Yao et al.: "Frequency-domain optical imaging of absorption and scattering distributions by a Born iterative method," J. Opt. Soc. Am. A., vol. 14, No. 1/Jan. 1997.
Yu et al.: "A phantom study of the geometric accuracy of computer tomographic and magnetic resonance imaging sterotactic localization with the Leksell stereotactic system", Neurosurgery, 2001, vol. 48, Issue 5, pp. 1092-1098.
Chao et al.: "Handbook of Accelerator Physics and Engineering", p. 30-31 (World Scientific), Sep. 1998.
European Extended Search Report for EP Application No. 11742922.5, dated Feb. 18, 2015.
Fermi National Accelerator Laboratory, "Design of a Proton Therapy Synchrotron" Jun. 1986, LL467-LL574.
Izumi et al.: "High Energy X-ray Computor Tomography for Industrial Applications," IEEE Transactions on Nuclear Science, vol. 40, No. 2, pp. 158-161, Apr. 2, 1993.
Menichelli et al.: "Development of a Proton Computed radiography Apparatus," 2008 IEEE Nuclear Science Symposium Conference Record, Oct. 19, 2008, pp. 5600-5608.
Paganetti, et al.: "Proton Beam Radiotherapy—The State of the Art," AAPM 47th Annual Meeting, Seattle, WA, Jul. 25, 2005, in 36 pages.
Slater, James M. et al., "The Proton Treatment Center at Loma Linda University Medical Center: Rationale for and Description of its Development", I.J. Radiation Oncology Biol. Phys. vol. 22, pp. 383-389, 1992.
International Invitation to Pay Additional Fees in PCT/US2011/024644, dated May 31, 2011.
International Preliminary Report on Patentability in PCT/US2011/024644, dated Aug. 23, 2012.
Israeli Office Action, in IL Application No. 221397, dated Aug. 24, 2016.

* cited by examiner

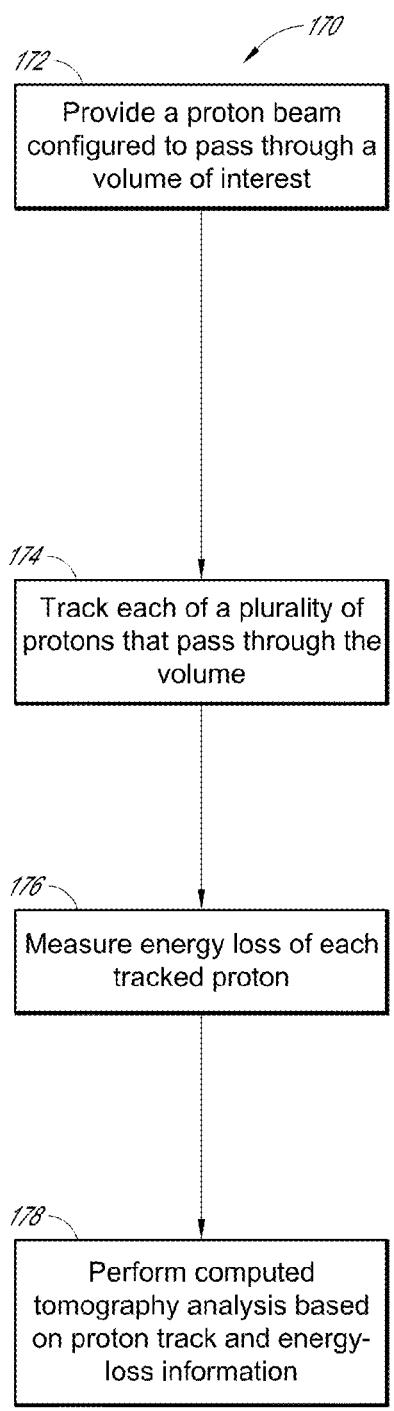
FIG. 5
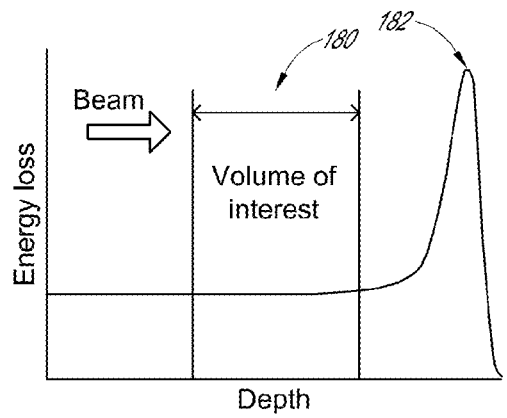
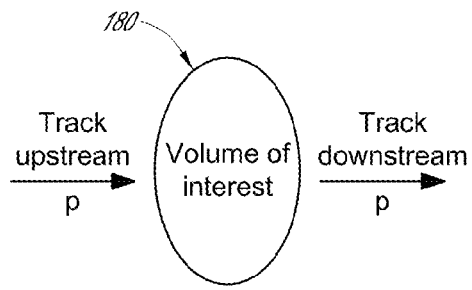
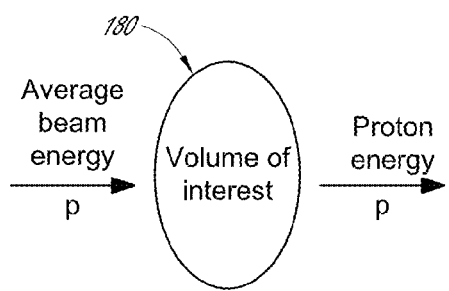
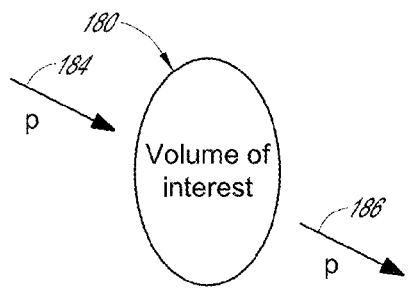
FIG. 6

SYSTEMS AND METHODOLOGIES FOR PROTON COMPUTED TOMOGRAPHY

STATEMENT REGARDING FEDERALLY SPONSORED R&D

This invention was funded, in part, by government support under NIH Grant No. R01HL070472 awarded by the National Heart, Lung, and Blood Institute. The government has certain rights in the invention.

INCORPORATION BY REFERENCE TO ANY PRIORITY APPLICATIONS

Any and all applications for which a foreign or domestic priority claim is identified in the Application Data Sheet as filed with the present application are incorporated by reference under 37 CFR 1.57 and made a part of this specification.

BACKGROUND

Field

The present disclosure generally relates to the field of medical imaging, and more particularly, to systems and methodologies for proton computed tomography.

Description of the Related Art

Computed tomography (CT) allows reconstruction of a specific physical property of a 3-dimensional object and arranges and displays this reconstruction as an array of 2-dimensional cross-sectional or "tomographic" images of the object. Such reconstruction can be facilitated by appropriately configured X-ray or particle radiation that penetrates the object. Detection of such radiation and processing of such data can facilitate reconstruction of such 2-dimensional images.

A proton beam can be configured to penetrate through an object. Reconstruction of 2-dimensional images from protons that pass through such an object can be difficult due to a relatively large number of protons involved and the different types of interactions that protons undergo within the object.

SUMMARY

In some implementations, the present disclosure relates to a method for performing computed tomography. The method includes obtaining measured data for a plurality of protons that pass through an object. The measured data includes information about first and second tracks for each of the protons. The first and second tracks correspond to the proton's trajectories before and after its passage through the object, respectively. The measured data further includes information about an interaction quantity of each proton resulting from its passage through the object. The method further includes estimating a path taken by each proton within the object based at least in part on the first and second tracks. The method further includes arranging the interaction quantities and the estimated paths of the protons such that the passages of the protons through the object is represented as or representable as a system of equations $Ax=b$ where $x$ is a distribution of a parameter associated with the object, $b$ represents the interaction quantities of the protons resulting from interactions along their respective paths in the object, and $A$ is an operator that operates on $x$ to yield $b$. The operator $A$ includes information about the estimated paths of the protons in the object. The system of equations can be configured so as to have a plurality of solutions. The method further includes estimating an initial solution for the system of equations. The method further includes seeking one or more feasible solutions among the plurality of solutions, with each feasible solution obtained by perturbing an existing solution and having a superior characteristic for a quantity associated with a reconstruction of the object parameter distribution than another solution obtained without the perturbation of the existing solution. The method further includes calculating the object parameter distribution based on a selected one of the one or more feasible solutions.

In some implementations, the interaction quantity of the proton can include an energy loss of the proton resulting from its passage through the object. In some implementations, $b$ can represent integrated values of the interaction quantity along the estimated paths of the protons. In some implementations, the system of equations $Ax=b$ can be a system of linear equations. In such a system, the operator $A$ can be a matrix.

In some implementations, the selected feasible solution can include a feasible solution that is not an optimal solution among the plurality of solutions. In some implementations, the calculating of the object parameter distribution can include calculating a 3D object parameter distribution. In some implementations, the method can further include forming an array of tomographic images of the object based on the calculated object parameter distribution.

In some implementations, the object parameter distribution can include a distribution of an electron density-based quantity. The electron density-based quantity can include relative proton stopping power with respect to a substantially uniform material such as water. In some implementations, the reconstructed object parameter distribution can include a 3-dimensional distribution of the electron density-based quantity.

In some implementations, the estimating of the path can include estimating a most likely path of the proton. In some implementations, the quantity associated with the reconstruction of the object parameter distribution can include a total variation of the reconstructed object parameter distribution. The superior characteristic of the total variation can include a lower value of the total variation.

In some implementations, the estimating of the initial solution can include calculating a filtered backprojection reconstruction solution.

In some implementations, the seeking of the one or more feasible solutions includes performing an iteration of perturbing a vector representation $x^k$ of the object parameter distribution $x$ so as to yield a perturbed vector $y^k$; evaluating the quantity associated with the reconstructed object parameter distribution associated with the perturbed vector $y^k$; and if the quantity associated with the perturbed vector $y^k$ is superior to the quantity associated with the unperturbed vector $x^k$, projecting $y^k$ so as to yield a next vector representation $x^{k+1}$.

In some implementations, the perturbing of the vector $x^k$ can include calculating $y^k$ such that $y^k = x^k + \beta_k v^k$, where $\beta_k$ is representative of a perturbation magnitude and $v^k$ is a perturbation vector. In some implementations, the quantity associated with the perturbed vector $y^k$ is superior with respect to the quantity associated with the unperturbed vector $x^k$ if the quantity evaluated for $y^k$ is less than or equal to the quantity evaluated for $x^k$. In some implementations, the projecting can include calculating $x^{k+1}$ as a mathematically-defined projection of $x^k$ onto some relevant convex set. The projecting can include projecting onto hyperplanes, half-spaces, hyperslabs, or other convex sets using a block-iterative projection algorithm such that the measured data is divided into a plurality of blocks. In some implementations, the projecting can include projecting using a diagonally relaxed orthogonal projection (DROP) based algorithm configured to allow diagonal component-wise relaxation in conjunction with orthogonal projections onto individual hyperplanes of the system. In some implementations, the DROP based algorithm can include a diagonally relaxed orthogonal matrix $\lambda_k U_{t(k)}$, where $\lambda_k$ is a relaxation parameter for the k-th iteration and $U_{t(k)}$ is a diagonal matrix with diagonal elements $\min(1, 1/h^t_j)$ for the t-th block and $h^t_j$ being a number of proton histories in the t-th block that intersect with a j-th voxel of the vector $x^k$.

In some implementations, the projecting can be performed cyclically through the blocks until all of the blocks are processed before proceeding to the next iteration. In some implementations, iteration can be performed for each block so that for a given block being processed, the projecting is performed only for the given block.

In some implementations, the present disclosure relates to a method for performing proton computed tomography. The method includes obtaining measured data for a plurality of protons that pass through an object. The method further includes applying a projection based reconstruction algorithm in iterations based on total variation superiorization to the measured data so as to yield a distribution of relative stopping power of the object. In some implementations, the method can further include forming a visual image of the object based on the relative stopping power distribution.

In some implementations, the present disclosure relates to proton computed tomography system. The system includes a proton delivery system configured to deliver a plurality of protons having a selected average energy sufficient to pass through an object. The system further includes a detector system configured to measure, for each of the protons, trajectories before and after the object and energy after passing through the object. The system further includes a data acquisition system configured to read out signals from the detector system so as to yield measured data representative of the trajectories and the energy of each of the protons. The system further includes a processor configured to process the measured data and perform an image reconstruction so as to yield a computed tomography image of the object. The image reconstruction includes projection based reconstruction algorithm in iterations based on total variation superiorization.

In some implementations, the present disclosure relates to a proton therapy system. The system includes a proton delivery system configured to deliver a beam of protons having a first average energy and a second average energy. The first average energy is selected such that a first Bragg peak occurs at a location within a target region inside a portion of a body. The second average energy is selected such that the beam of protons passes through the portion of the body. The system further includes a first detector system configured to facilitate the delivery of the first-energy beam to the target region. The system further includes a second detector system configured to measure, for each of the protons having the second energy and passing through the portion of the body, trajectories before and after the portion of the body and energy after passing through the portion of the body. The system further includes a data acquisition system configured to read out signals from at least the second detector system so as to yield measured data representative of the trajectories and the energy of each of the second-energy protons. The system further includes a processor configured to process the measured data and perform an image reconstruction so as to yield a computed tomography image of the portion of the body. The image reconstruction includes projection based reconstruction algorithm in iterations based on total variation superiorization.

In some implementations, the present disclosure relates to a tangible computer readable storage medium having computer-executable instructions stored thereon, where the computer-executable instructions are readable by a computing system having one or more computing devices, and the computer-executable instructions are executable on the computing system in order to cause the computing system to perform operations that include obtaining data about a plurality of protons. The data includes information about first and second tracks for each of the protons. The data further includes information about energy loss of each proton between the first and second tracks. The operations further include estimating a path between the first and second tracks for each proton. The operations further include performing a tomography analysis of relative stopping power distribution based on the energy losses and the paths of the protons using projection based reconstruction algorithm in iterations based on total variation superiorization.

In some implementations, the present disclosure relates to a particle radiation therapy system. The system includes a particle radiation delivery system configured to deliver a beam of ions having a first average energy and a second average energy. The first average energy is selected such that a first Bragg peak occurs at a location within a target region inside a portion of a body. The second average energy is selected such that the beam of ions passes through the portion of the body. The system further includes a first detector system configured to facilitate the delivery of the first-energy beam to the target region. The system further includes a second detector system configured to measure, for each of the ions having the second energy and passing through the portion of the body, trajectories before and after the portion of the body and energy after passing through the portion of the body. The system further includes a data acquisition system configured to read out signals from at least the second detector system so as to yield measured data representative of the trajectories and the energy of each of the second-energy ions. The system further includes a processor configured to process the measured data and perform an image reconstruction so as to yield a computed tomography image of the portion of the body. The image reconstruction includes projection based reconstruction algorithm in iterations based on total variation superiorization.

In some implementations, the ions include protons. In some implementations, the ions include carbon ions.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 5 shows a process for performing tomography based on characterization of protons that pass through a volume of interest, where information obtained from such tomography can be utilized in a number of applications such as the identification of the desired target.

FIG. 6 schematically shows examples of proton beam configurations and detections of such protons that pass through the target so as to facilitate the tomography process of FIG. 5.

DETAILED DESCRIPTION OF SOME EMBODIMENTS

The headings provided herein, if any, are for convenience only and do not necessarily affect the scope or meaning of the claimed invention.

Described herein are methodologies and related systems for performing computed tomography (CT) using protons as interacting radiation. It will be understood that although the description herein is in the context of protons, one or more features of the present disclosure can also be implemented in CT applications using other positive-charged ions as well.

Figure 1A:
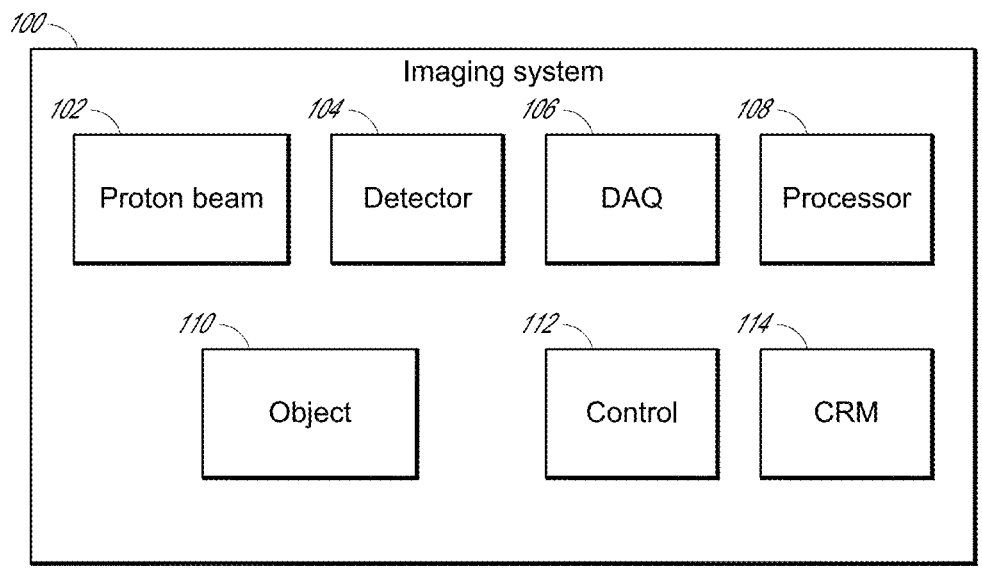
FIG. 1A schematically shows that in some implementations, a proton computed tomography (pCT) system can be configured as an imaging system.
Figure 1B:
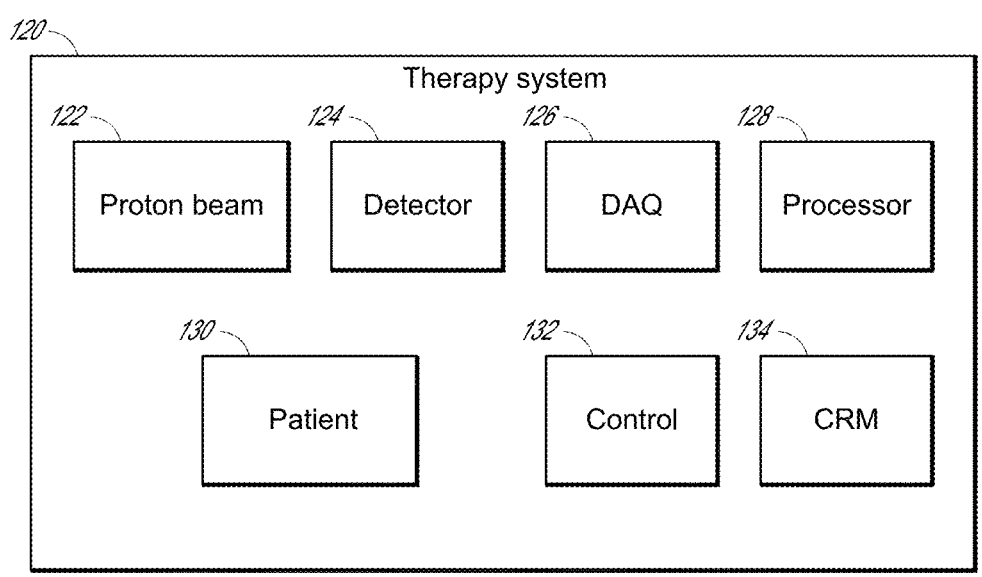
FIG. 1B schematically shows that in some implementations, a pCT system can be configured to facilitate treatment of patients using a proton therapy system.

FIG. 1A shows that in some embodiments, an imaging system 100 can be configured to perform proton computed tomography (pCT) operations and yield data that can be represented as a CT image of one or more portions of an object 110. The imaging system 100 can include a proton beam component 102 configured to deliver a beam of protons to the object 110. Controlling of various parameters of the proton beam, such as energy, direction and intensity can be achieved in a number of known ways.

The imaging system 100 can further include a detector component 104 configured to characterize protons that are incident on the object 110 as well as those that have passed through the object. In some implementations such a detector component 104 can be configured to be capable of characterizing single protons. Examples of devices that can facilitate such characterization of protons are described herein in greater detail.

The imaging system 100 can further include a data acquisition (DAQ) component 106 configured to read out signals from the detector component 104 so as to facilitate CT analysis. Amount of signal processing performed by the DAQ component 106 can vary.

In some implementations, signals from various detectors can be converted to digital signals by one or more analog-digital-converters (ADCs), and such digital signals can be read out under the control of a control component 112. Various control parameters such as event triggering, timing of event signals and readout, and resetting of detectors can also be controlled by the control component 112.

In some implementations, the imaging system 100 can further include a processor 108 that is configured to receive the digitized signals and perform analyses such as tracking of protons upstream and downstream of the object 110, as well as calculation of energies of downstream protons that passed through the object 110. In some implementations, tomographic reconstruction processing can also be performed by the processor 108. In other implementations, such tomographic reconstruction processing can be performed by a separate processor.

In some implementations, the imaging system 100 can further include a computer readable medium 114 configured to store information and/or executable instructions that facilitate operation of one or more components of the system 100. In some implementations, the computer readable medium 114 can include information and/or executable instructions that facilitate performance of one or more reconstruction processes as described herein. In some implementations, such information and/or executable instructions can be stored in a non-transitory manner.

In some implementations, one or more features of the present disclosure can be incorporated into a radiation therapy system 120 such as a proton or carbon beam therapy system. The therapy system 120 can include a proton or carbon beam component 122 configured to deliver a beam of protons or carbon ions to a patient 130. Such a beam of protons or carbon ions can be configured to yield a therapeutic effect on the patient. In certain implementations, the proton beam component 122 can also be configured to yield proton beams that can pass through the patient so as to allow tomographic analysis as described above in reference to FIG. 1A. Examples of how such beams can be provided are described herein in greater detail.

The imaging system 120 can further include a detector component 124 configured to facilitate the treatment utilization of the proton beam. Such a detector component 124 can include devices that are configured to characterize protons that are incident on the patient 130 with desired parameters such as energy, direction and intensity. Such devices can be implemented in a number of known ways.

In some implementations, the detector component 124 can further include devices that are configured to facilitate pCT imaging functionalities such as those described in reference to FIG. 1A. In some embodiments, at least some of the therapy related detection devices can also be utilized for the purpose of pCT imaging. For example, beam detectors upstream of the patient can be utilized to characterize individual protons incident on the patient during operation in an imaging mode.

The imaging system 120 can further include data acquisition (DAQ) 126, control 132, processor 128 and computer readable medium 134 components configured to facilitate therapeutic and/or imaging modes of operation.

Appropriately configured proton or carbon ion radiation (i.e., charged particle radiation) can provide a number of benefits in therapeutic applications such as certain cancer treatments. One of such benefits can be attributed to a sharp energy loss at the end of travel of a proton in a given material. Such a sharp energy loss has a relatively sharp peak called a Bragg peak; and very few of the particles (with same beam energy) penetrate beyond such a depth. Depth locations of such Bragg peaks can depend on the particle beam energy. Generally, a deeper Bragg peak can be achieved by a higher energy particle beam. Protons used for therapy can have energies in a range of about 70 MeV to 250 MeV and carbon ions up to 430 MeV/atomic mass unit.

Figure 2A:
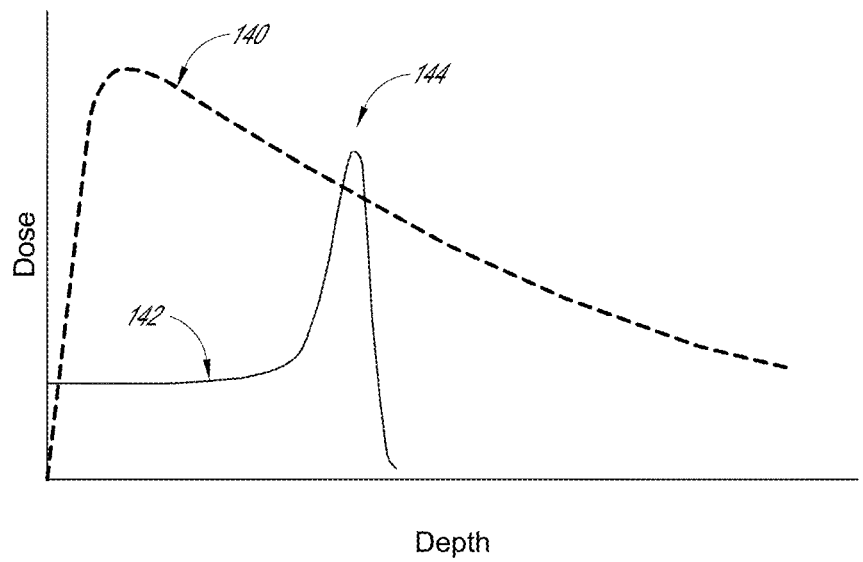
FIGS. 2A and 2B show example dose profiles for photon and proton therapies, where protons can be configured to provide a more selective dose delivery in a desired region being targeted.

FIG. 2A shows an example of a Bragg peak 144 of an energy loss profile 142 as a function of depth as an energetic proton travels in a given material (e.g., tissue). In comparison, a relative dose profile 140 for an electromagnetic radiation (e.g., X-ray or gamma ray) has a relatively sharp rise to a maximum followed by a gradual decrease as a function of depth. Accordingly, photon-based radiation does not provide a similar end-range control provided by use of protons and carbon ions.

Figure 2B:
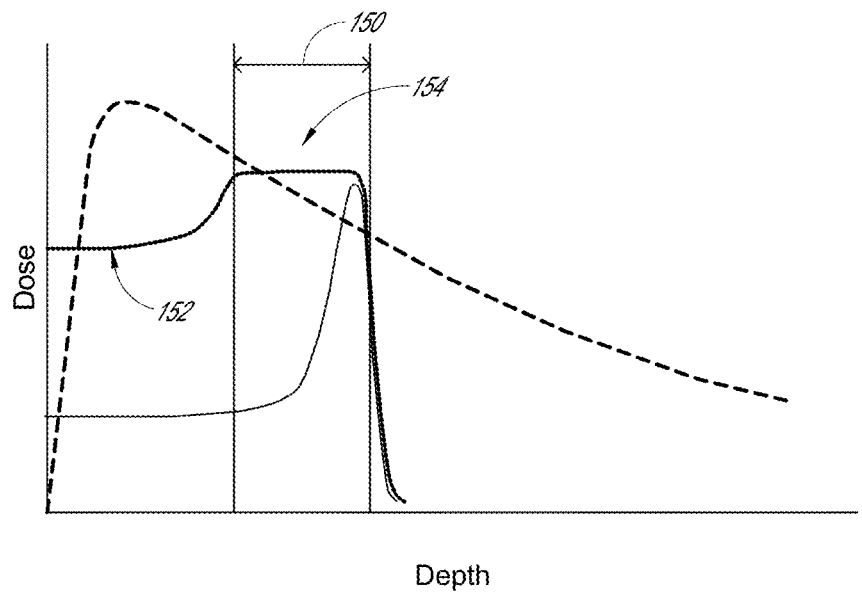

FIG. 2B shows that a plurality of pristine Bragg peaks can combine to yield a spread out Bragg peak (SOBP) 154 in a cumulative dose profile 152. Such pristine Bragg peaks can be achieved by subjecting the same volume with proton beams having different energies. The location of the resulting spread out Bragg peak 154 can be selected to overlap with the depth boundaries of a target region 150. If the beam energies are properly selected, the spread out Bragg peak can fall off sharply beyond the distal boundary of the target region.

Figure 3A:
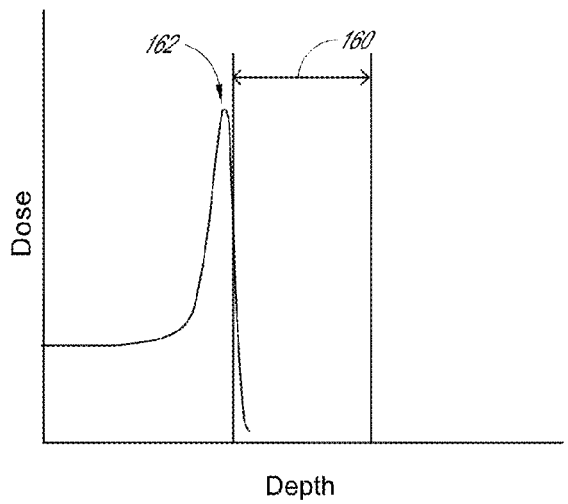
FIGS. 3A and 3B show that wrong calculations of protons' Bragg peak locations relative to the desired target can result in undesirable irradiation of regions outside of the target.
Figure 3B:
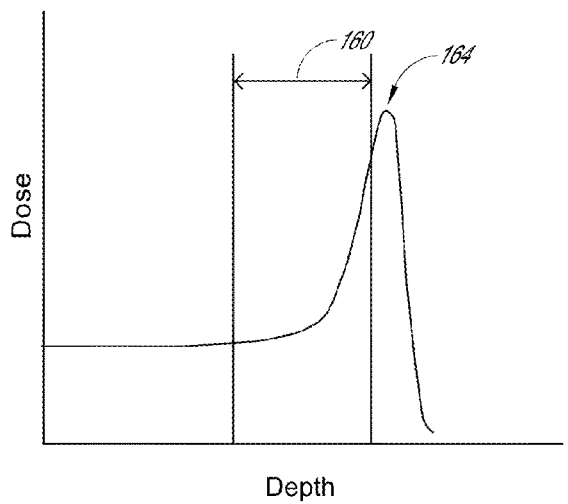

Based on the foregoing, proper matching of depth boundaries of a target region with a spread out Bragg peak can be an important particle therapy consideration. If the distal portion of the spread out Bragg peak is too deep, such as in an example of FIG. 3A, unnecessary and harmful radiation dose (e.g., a substantial portion of a Bragg peak 164) is provided to a region beyond the distal boundary of the target region 160. If the proximal portion of the spread out Bragg peak is too shallow, such as in an example of FIG. 3B, unnecessary extra radiation dose (e.g., a substantial portion of a Bragg peak 162) is provided to a region in front of the proximal boundary of the target region 160. On the other hand, a proximal portion of the spread out Bragg peak that is too deep, and/or a distal portion of the spread out Bragg peak that is too shallow, may result in certain portions of the target region not being irradiated properly.

Figure 4:
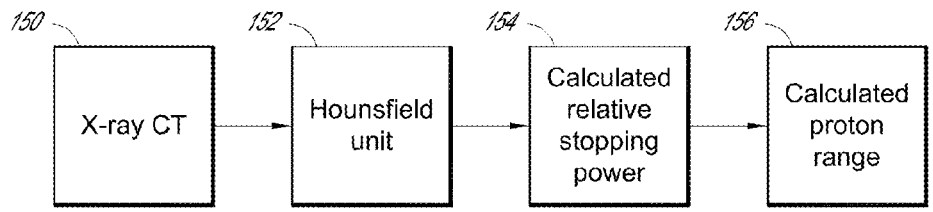
FIG. 4 schematically shows how proton ranges can be adjusted for treatment, based on identification of the desired target using X-ray computed tomography (CT).

The foregoing uncertainty of proton penetration depth in a given medium can result from characterization of the medium with a different probe radiation that interacts differently with the medium. FIG. 4 shows a typical process that can be used for determining a range of a proton beam having a given energy and traversing a given medium. A similar process can be applied for a carbon ion beam with a difference being that instead of relative stopping power for protons, relative stopping power for carbon ions (which can be estimated by multiplying the proton stopping power for protons by the squared atomic number ratio $(Z_C/Z_p)^2=36$) is used. An X-ray CT can be performed on an object (e.g., a patient) (block 150) so as to obtain an image based on attenuation coefficient measurements of the object. Such measurements can be converted to a Hounsfield unit scale (block 152). Calculated relative stopping power of protons or carbon ions in the medium can be obtained based on the Hounsfield scale measurements (block 154). Since the proton or carbon ion range can be expressed as a function of beam energy and the relative stopping power of the material for protons or carbon ions, calculated proton or carbon ion range can be obtained (block 156).

The foregoing process of calculating proton range from X-ray CT measurements can yield an uncertainty of about 3.5% of a proton's or carbon ion's range. Such a relative uncertainty can equate to different distances for different portions of a human body. For example, the 3.5% relative uncertainty equates to about 3-5 mm in brain, and about 10-12 mm in pelvis. Additional uncertainties can be introduced due to presence of materials with unknown densities, as well as streak artifacts in the X-ray CT images.

In some implementations, proton or carbon ion range determination based on pCT techniques as described herein can reduce the range uncertainty to about 1% or less of the proton's range. FIG. 5 shows a process 170 that can be implemented to perform proton computed tomography. FIG. 6 shows example configurations that can be implemented for the process 170 of FIG. 5.

In block 172, a proton beam can be provided to an object having a volume of interest. In some implementations, the beam can be configured so that a substantial portion of protons in the beam pass through the object. For example, and as shown in FIG. 6, the proton beam can be provided with energy so that the resulting Bragg peak 182 would occur past the distal boundary of a volume of interest. In some implementations, the object being imaged can define the volume of interest. In such situations, protons can pass through the entire object and be detected downstream of the object.

In block 174, each of a plurality of protons that pass through the volume can be tracked. For example, and as shown in FIG. 6, such tracking can include tracking of protons that are upstream and downstream of the volume of interest 180. Examples of such tracking are described herein in greater detail.

In block 176, energy loss of each tracked proton can be measured. For example, and as shown in FIG. 6, such energy measurement can include measurement of an average beam energy for protons that are upstream of the volume 180, and measurement of each downstream proton by an energy detector such as a calorimeter. Examples of such an energy measurement are described herein in greater detail.

In block 178, computed tomography analysis can be performed based on the protons' track and energy-loss information. For example, and as shown in FIG. 6, such a CT analysis can be facilitated by measuring such information about protons incident (184) on and passing through (186) the volume 180 at a number of different orientations. Examples of such orientation changes are described herein in greater detail.

Figure 7:
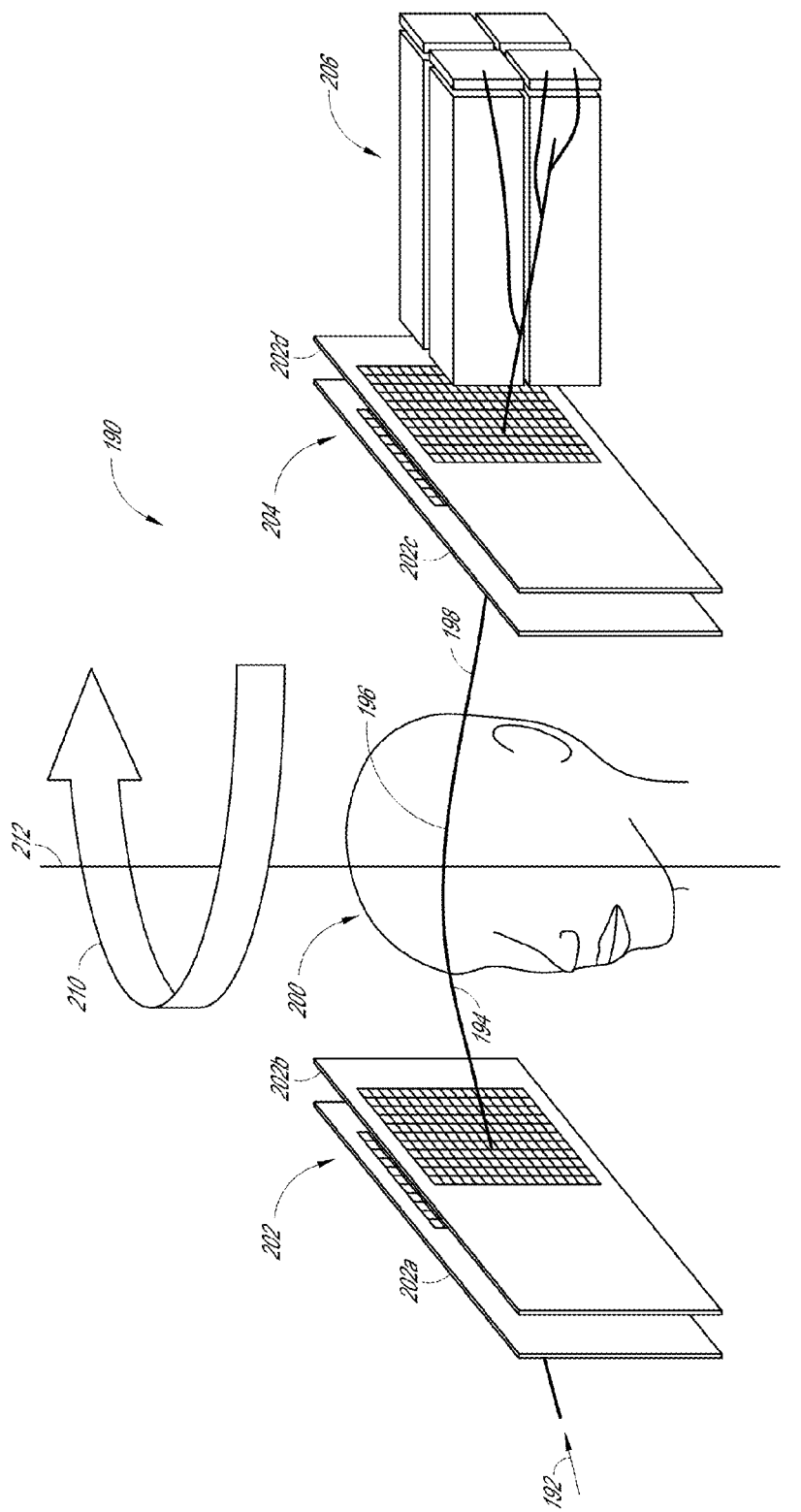
FIG. 7 shows that in some implementations, a pCT system can include detectors configured to be capable of tracking and determining energy loss of a single proton passing through a target, where such measurements can be performed at a plurality of orientations relative to the target so as to allow tomographic reconstruction of an image of at least a portion of the target.

FIG. 7 shows that in some embodiments, an assembly of detectors can be configured so as to allow measurement of individual protons incident on an object (e.g., a portion of a patient) 200 and after having passed through the object 200. For example, a single proton 192 is depicted as being incident (194) on the object 200, traversing (196) the object 200, and having passed through (198) the object 200.

In some implementations, an upstream detector 202 can provide incident track (194) information for the proton 192, and a downstream detector 204 can provide downstream track (198) information for the proton 192. As described herein, the path 196 that the proton takes as it traverses the object 200 can be estimated so as to facilitate the CT analysis.

The upstream and downstream tracking detectors 202, 204 can be implemented in a number of ways. The upstream tracking detector 202 can be configured to allow determination of a spatial vector and location of the proton when it enters the object 200. Similarly, the downstream tracking detector 204 can be configured to allow determination of a spatial vector and location of the proton when it exits the object 200. Based on such information, the traversing path 196 can be estimated as described herein.

In some implementations, each of the upstream and downstream tracking detectors 202, 204 can include two or more 2D-position sensitive detection planes. For example, the upstream detector 202 can include two 2D-position sensitive detection planes 202a, 202b; and the downstream detector 204 can include two 2D-position sensitive detection planes 204a, 204b. Each of the 2D-position sensitive detection planes (202a, 202b, 204a, 204b) can include X and Y position sensitive planes implemented in a number of ways, including, for example microstrip detectors (e.g., silicon strip detectors). In some situations where tracking ambiguities may be likely (e.g., in high count environment), additional position sensitive planes (e.g., U and/or V planes) may be added or faster detectors and/or readout system can be used to reduce such ambiguities.

Referring to FIG. 7, the assembly of detectors can further include an energy detector 206 configured to detect the energy of a downstream proton. Such an energy detector can be implemented in a number of ways, including, for example, a multi-crystal based calorimeter. An example of such an energy detector is described herein in greater detail.

In certain implementations, a number of other detectors and/or devices can be included to provide various functionalities. For example, beam-defining counters that can identify and veto events involving double-particle or stray incident particles can be included. In another example, counters and circuits configured to define and trigger good events while rejecting spurious signals can also be included.

Referring to FIG. 7, such an assembly of detectors and/or the object 200 can be made to rotate about a selected axis so as to facilitate obtaining of proton data at a plurality of orientations for CT analysis. For example, the assembly of detectors can be configured to rotate (arrow 210) together about an axis 212 of the object 200.

Figure 8:
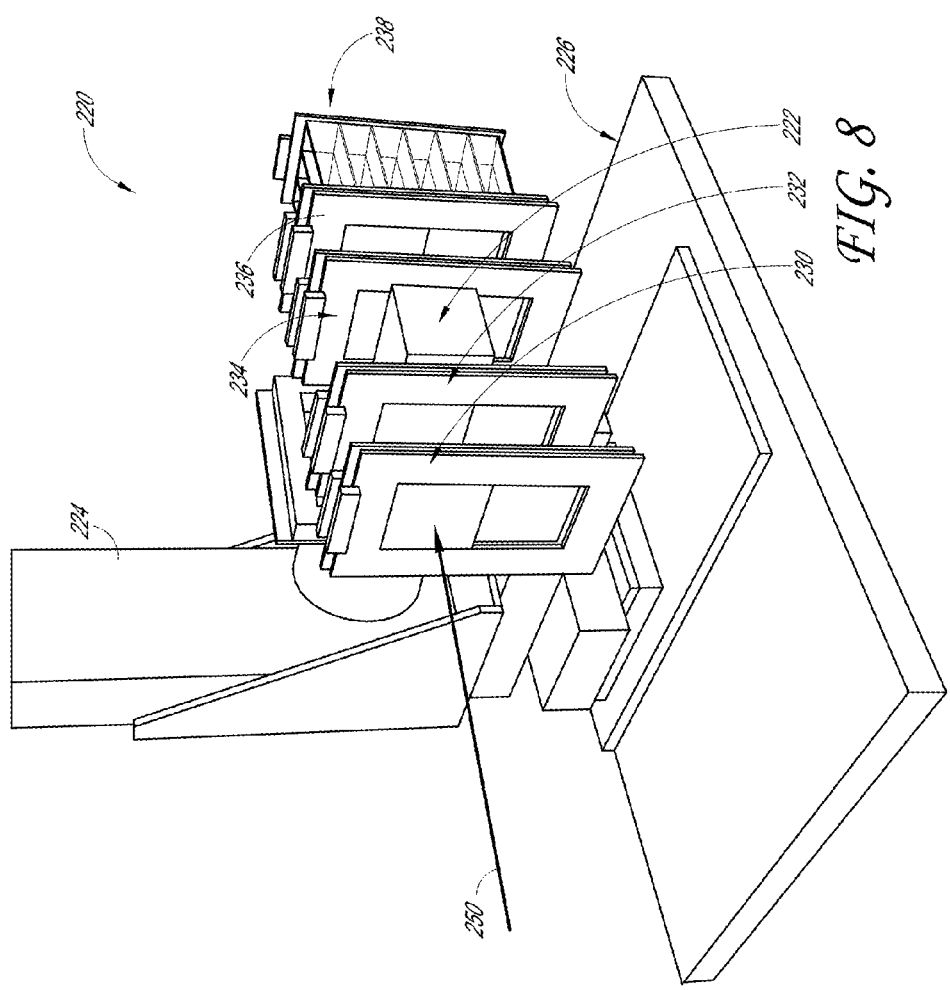
FIG. 8 shows an example platform for mounting the example pCT detectors of FIG. 7.

It will be understood that in other examples, the detectors, the object, or some combination thereof can rotate and/or translate to facilitate the CT functionality. For example, FIG. 8 shows a configuration 220 where an assembly of detectors (e.g., 2D-position sensitive detectors 230, 232, 234, 236 and energy detector 238) can be mounted to a platform 226 in a substantially fixed manner and oriented to receive a proton beam 250 and detect downstream protons. To provide CT functionality, an object 222 being characterized can be mounted to a mounting structure 224 so as to allow rotation of the object 222 about an axis. Such a configuration where the object rotates can be more appropriate where the object 222 is an inanimate object (e.g., a phantom) and the proton beam has a substantially fixed direction.

Figure 9:
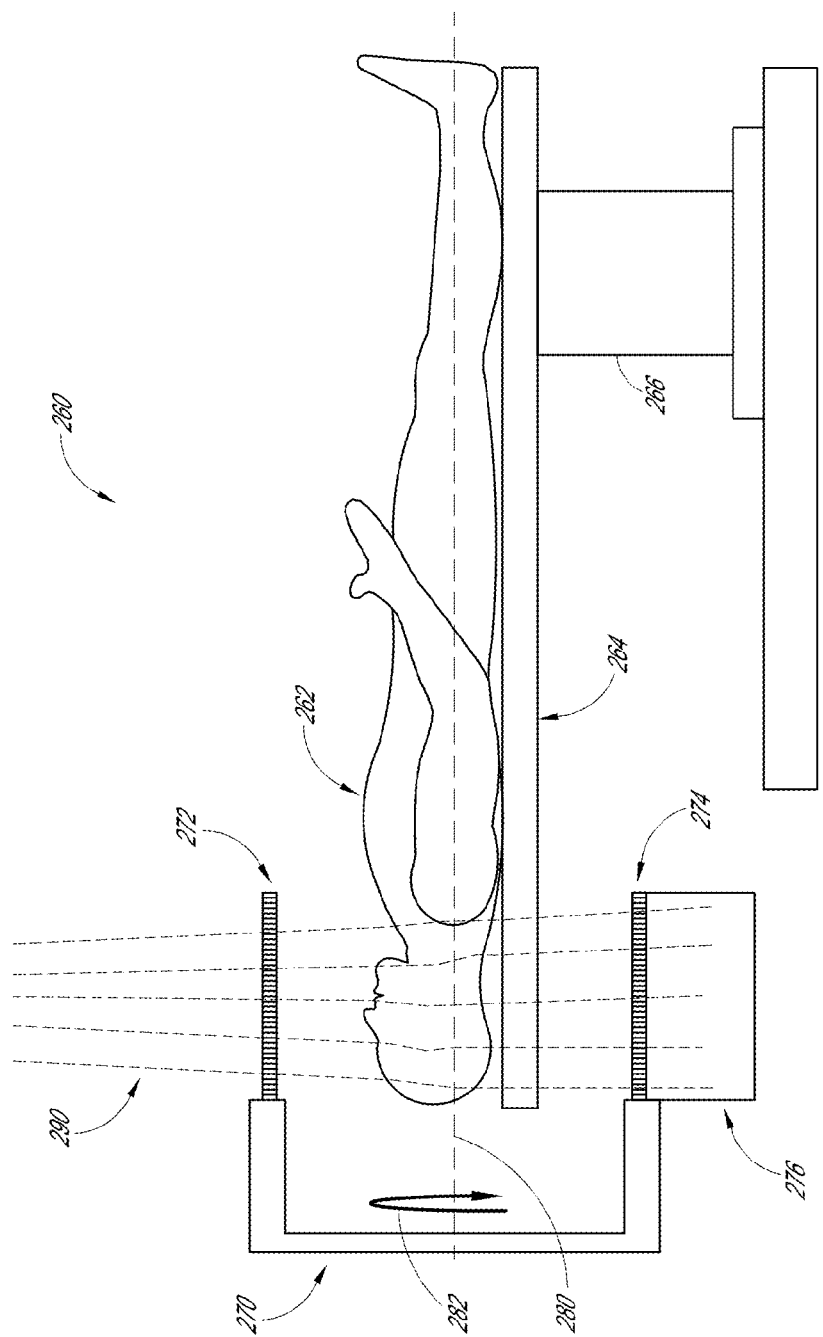
FIG. 9 shows an example system configured to perform pCT imaging of a subject such as a human being.

In another example, FIG. 9 shows a configuration 260 where an object 262 (e.g., a patient) is substantially stationary, and an assembly of detectors (e.g., upstream tracking detector 272, downstream tracking detector 274, and energy detector 276) can be configured to rotate about an axis 280 defined by the object 262.

The example detectors 272, 274, 276 can be mounted to a rotatable structure 270 that allows rotation (arrow 282) of the detector assembly about the axis 280. The stationary object 262 can be achieved by, for example, a support structure 264 mounted to a stable structure 266. In some embodiments, the support structure 264 can be configured to allow movement of the object in and out of the region where protons 290 travel between the upstream and downstream detectors 272, 274. Such a configuration where the detector assembly rotates about the object can be more appropriate where the object 262 is a living being such as a human patient.

In some implementations, some or all of the detectors of the example configuration 260 of FIG. 9 can be incorporated into proton therapy systems such as those having a treatment gantry design. In such a design, a patient can be moved in and out of a beamline. The beamline can rotate about the patient for a desired delivery of treatment protons.

For such systems, upstream and downstream detectors and energy detector can be mounted to the rotatable structure so as to rotate with the beamline. Such detectors can be fixed in place or be retractable so as to not interfere with the therapeutic operation. In some embodiments, the therapy system's beam control devices can provide some or all functionalities associated with the upstream tracking detector.

Figure 10:
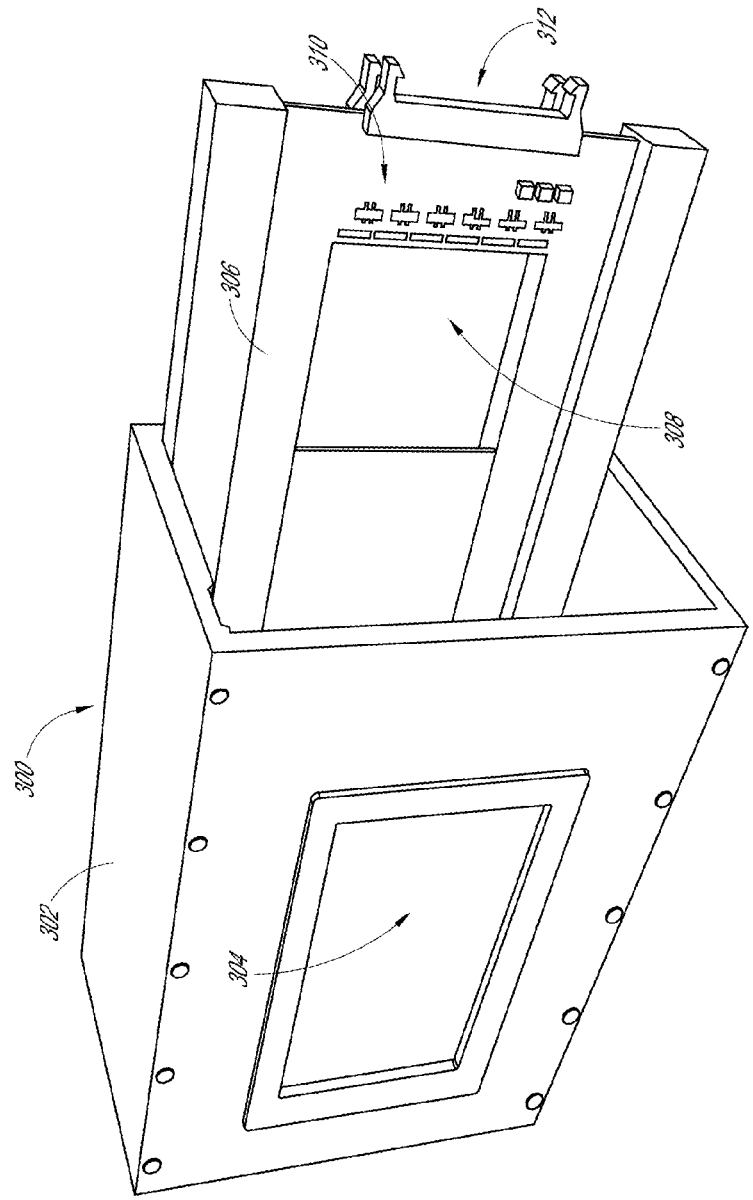
FIG. 10 shows a partially disassembled view of an example tracking detector configured to track single protons upstream or downstream of the target.

FIG. 10 shows an example tracker module 300 that can be utilized as an upstream or downstream tracking detector described in reference to FIGS. 7-9. A number of pCT results disclosed herein were obtained using such a device. As shown, the tracker module 300 can include a housing 302 configured to hold two or more 2D-position sensitive detectors. One of such a 2D-position sensitive detector 306 is shown in a partially removed manner, and the other 2D-position sensitive detector has been removed in FIG. 10.

The 2D-position sensitive detector 306 can include an active area 308 (e.g., a rectangle having silicon strip detecting elements), a circuit 310 for controlling of the detecting elements and reading out of signals therefrom, and an interface 312 for supplying power, control signals, readout signals, etc.

The housing 302 can include a window 304 that preferably aligns with the active area 308 of the 2D-position sensitive detector 306 (when installed) so as to allow passage of protons with a relatively low probability of interaction. When needed, such a window can include thin sheets of materials such as mylar.

The housing 302 can be configured to allow mounting of the module 300 to a support structure so as to allow the module 300 to be stationary (e.g., if the object is rotatable) or rotatable about the object (not shown).

Figure 11:
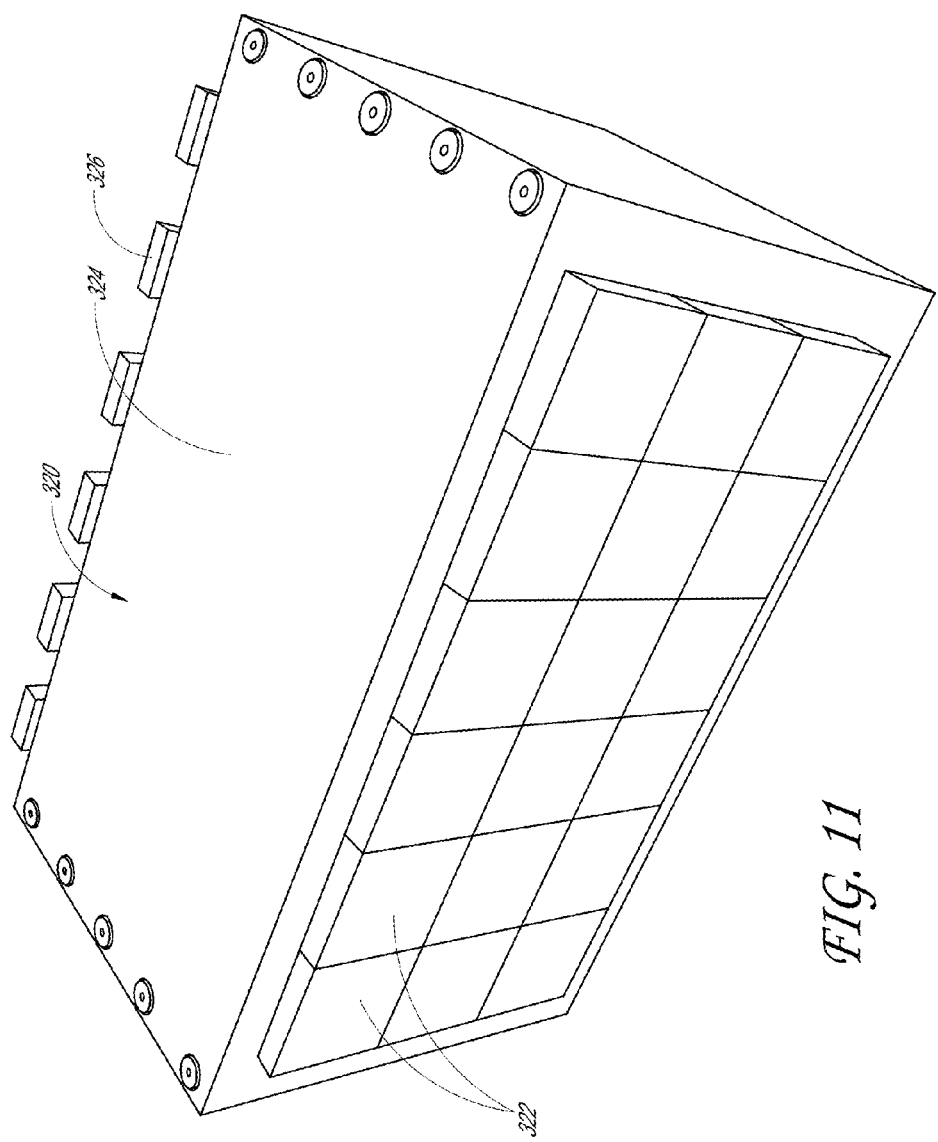
FIG. 11 shows an example calorimeter configured to be capable of measuring energy of a single proton.

FIG. 11 shows an example energy detector 320 that can be utilized in the examples described in reference to FIGS. 7-9. A number of pCT results disclosed herein were obtained using such a device. As shown, the energy detector 320 can include a plurality of detector crystals 322 (e.g., CsI crystals) arranged so as to provide segmented energy detection capability. In the example shown, the crystals 322 are packed in a grid array so as to provide a grid-like segmentation. Design parameters such as dimensions of the front face of the crystal 322 and depth of the crystal 322 can be selected to accommodate expected energy ranges and intensities of downstream protons.

Referring to FIG. 11, the back ends of the crystals 322 are depicted as being coupled to photo detectors 326. Such photo detectors can be implemented in a number of ways, including, for example, use of various types of photomultipliers. A number of other types of energy detector can also be utilized, including, for example, a solid state detector or a stack of organic or inorganic scintillators configured to detect ranges of the downstream protons.

In FIG. 11, the crystals 322 are depicted as being packed within a housing 324. Such a housing can be configured to allow mounting of the energy detector 320 to a support structure so as to allow the energy detector 320 to be stationary (e.g., if the object is rotatable) or rotatable about the object (not shown).

As described herein, proton's interactions within an object being characterized typically results in direction change and energy loss from the incident direction and incident energy, respectively. When passing through the object, a proton can experience multiple small-angle deflections due to scatterings at nuclear potential of the target atoms; and such deflections can result in a substantially random macroscopic deviation from the original direction. In some situations, such a deviation can be as much as few degrees that results in a significant displacement (e.g., up to a few millimeters) of the exit point (relative to a straight-line projection of the entry point and direction) on the distal end of the object.

Figure 12:
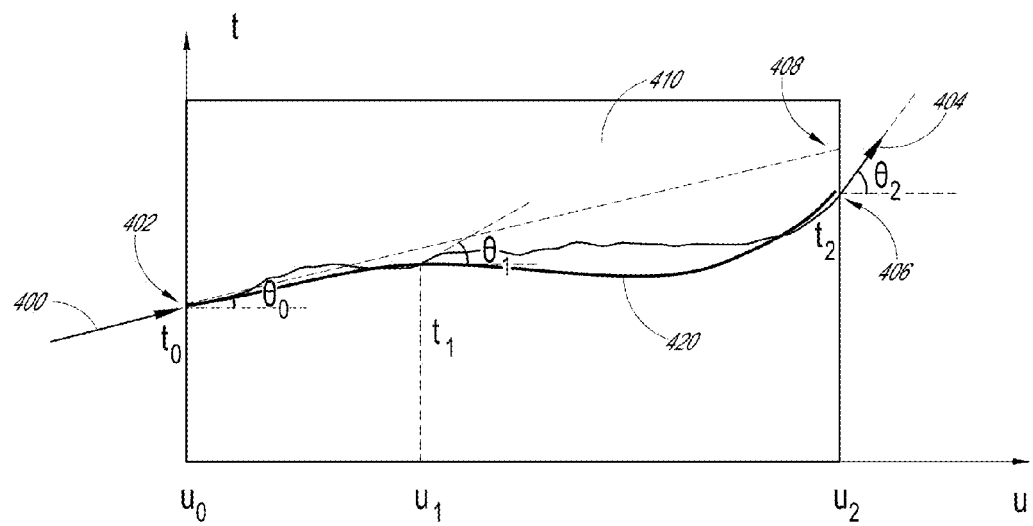
FIG. 12 shows an example of how a proton's path can deviate due to effects such as multiple-Coulomb scattering (MCS) within the target, and how a most likely path (MLP) can be estimated.

FIG. 12 depicts a two-dimensional representation of an example of such small-angle deflections as a proton with incident direction 400 and entry point 402 traverses an object 410 and exits with exit direction 404 and exit point 406. In the example, the exit direction has deviated from the entry direction; and similarly, and the exit point 406 has shifted from a projected point 408 where the proton would go if travelling in a straight line.

Such a multiple Coulomb scattering (MCS) effect can produce an uncertainty in the proton's trajectory L. Because such a trajectory can contribute to spatial resolution of a proton CT image, an accurate estimation of the trajectory is desirable. In some target objects, there is no direct information about proton's actual path within the object. However, there are a number of techniques for estimating a most likely path within the object, given knowledge of the proton's paths before and after the object. For example, a semi-analytical calculation can be performed on Gaussian approximation of multiple scattering. In another example, a set of Monte Carlo simulations can be performed based on a given configuration that can include factors such as object size, object material, beam energy and detected proton paths and energy.

In FIG. 12, a most likely path (MLP) corresponding to the incident and exit paths 400, 404 is depicted as a curved line 420; and such a trajectory can be used for CT reconstruction.

In some implementations, the foregoing path deviations resulting from effects such as multiple Coulomb scattering can render some image reconstruction algorithms less effective. For example, filtered back projection (FBP) is a common reconstruction method used in X-ray CT systems, and assumes that the photons travel in straight lines inside an object being characterized.

Figure 13:
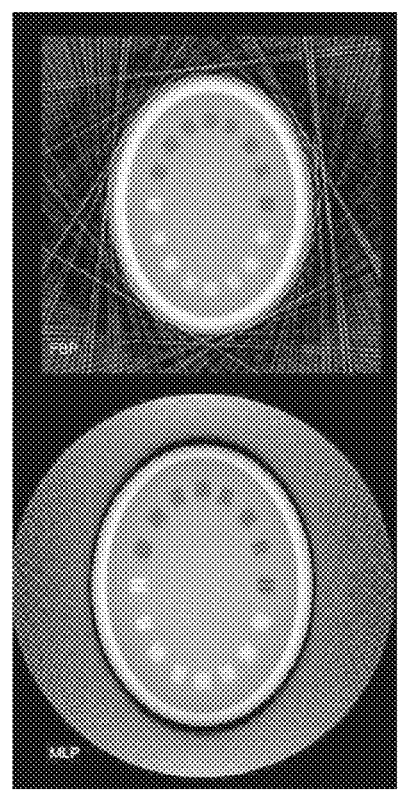
FIG. 13 shows a comparison between a reconstructed image based on an assumption that proton paths are straight, and a reconstructed image incorporating the MLP of the protons.

When such a methodology is utilized for proton CT image reconstruction, image quality suffers significantly. FIG. 13 shows proton CT images, where the upper image was obtained using the FBP method and the lower image was obtained by incorporating the MLP. One can see that in general, the FBP image has a lower quality than the MLP image. For example, significant portions of the FBP image are blurred.

As a proton traverses a medium along its trajectory L, it undergoes energy loss due to its interactions with the medium. The following integral contains this energy loss $$\int_{E_{out}}^{E_{in}} \frac{dE}{S_{water}(E)}$$

where $E_{in}$ and $E_{out}$ represent incident and exit energies, respectively, and $S_{water}(E)$ represents an energy-dependent proton stopping power function in water. Further, such an integral can be set to be substantially equal to the integral of relative electron density or relative proton stopping power along the proton path, such that $$\int_{E_{out}}^{E_{in}} \frac{dE}{S_{water}(E)} = \int_{Path} \eta_e(u) du. \quad (1)$$

In some implementations, the proton path can be approximated as a most likely path (MLP).

For a given detected proton, the left side of Equation 1 can be determined since the proton's incident and exit energies are measured. Thus, knowing the MLP of the proton allows the relative stopping power $\eta_e$, which is closely related to the electron density of the object, to be calculated along the MLP. Given sufficient number of such protons, the relative stopping power function $\eta_e$ can be calculated for a region of interest in the object being characterized. Such a function $\eta_e$ can be determined with sufficient details so as to allow generation of a high quality image.

Figure 14:
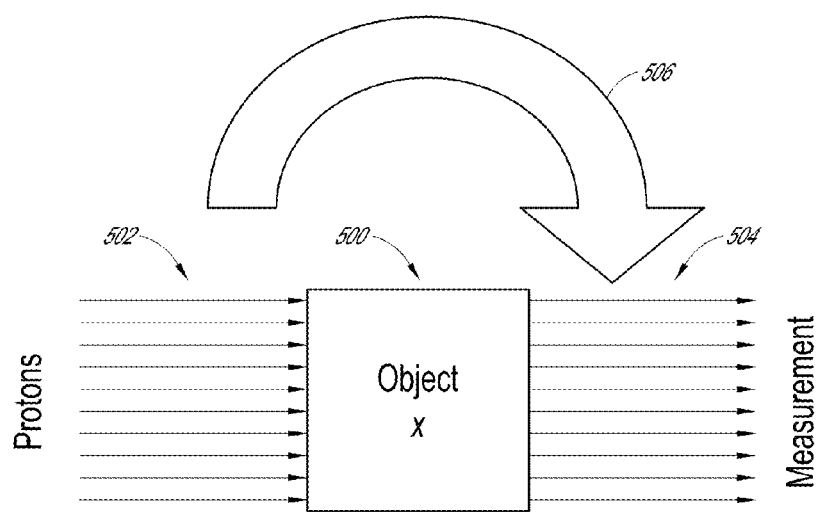
FIG. 14 schematically depicts an example reconstruction methodology for characterizing an object based on measurement of protons that pass through the object.

FIG. 14 shows that in some implementations, a plurality of input protons 502 traversing and interacting with an object 500 so as to yield output protons 504 can be represented as a transformation 510 M·x=g, where x is a 3-dimensional distribution of an interaction parameter (e.g., electron density or electron-density-based quantity such as relative stopping power (RSP)) associated with the object, M is an operator that operates on x so as to yield g, and g represents measured data. Thus, the object function x can be determined as x=M$^{-1}$·g, where M$^{-1}$ is an inverse of M. As described herein, an inverse of an operator can be appropriate when the operator is, for example a square matrix. It will be understood that such a square matrix is not a requirement. In situations where the operator matrix is a more general rectangular matrix, the object function x can be determined as x=M$^{\dagger}$·g, where M$^{\dagger}$ ("M dagger") is a conjugate transpose of M. It will be understood that similar notations can apply to other operators (e.g., operator A in FIG. 15) described herein.

Figure 15:
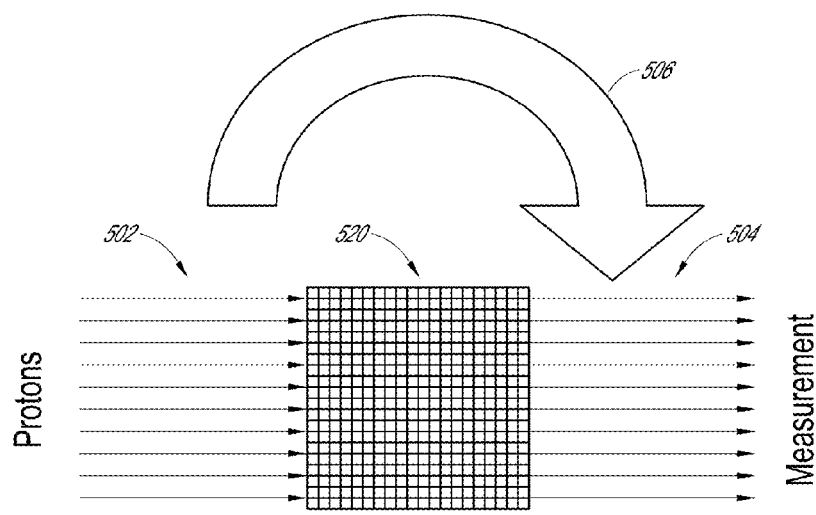
FIG. 15 schematically depicts an example discrete approach to the reconstruction methodology of FIG. 14.

FIG. 15 shows that in some implementations, the general form of transformation of FIG. 14 can be approximated as a discrete transformation 522 where an object 520 is digitized into a vector. Such a transformation can be represented as A·x=b, where x is a discrete object vector, A is an operator that operates on x so as to yield b, and b represents a vector of measured data. Thus, the object vector x can be determined as x=A$^{-1}$·b, where A$^{-1}$ an inverse of A.

In some implementations, the discrete transformation 522 of FIG. 15 can represent a system of linear equations, such that the object vector x is a column vector having n elements $x_1, x_2, x_3, \ldots, x_n$, the measurement vector b a column vector having m elements $b_1, b_2, b_3, \ldots, b_m$, and the transformation operator A an m×n matrix.

Figure 16:
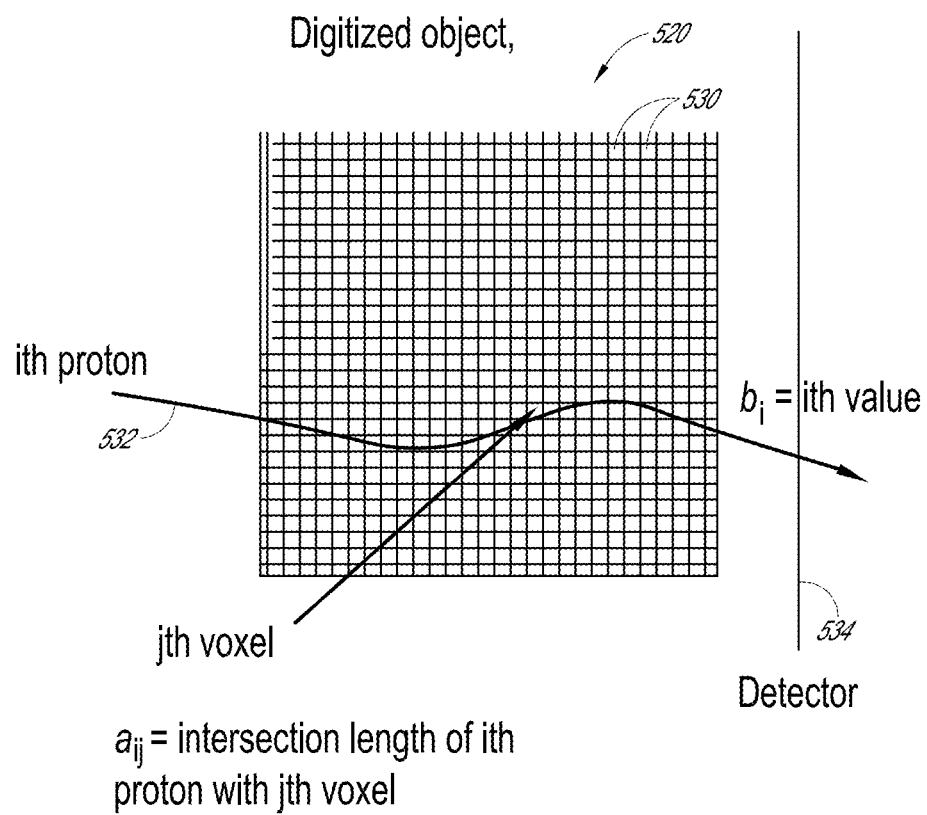
FIG. 16 shows a more detailed example of the discrete approach of FIG. 15.

FIG. 16 shows an example of the digitized object 520 that can be represented as the object vector x. The object 520 is depicted as having a plurality of voxels 530. An i-th proton 532 is depicted as traversing the digitized object 520 so as to intersect a number of voxels 530 along its path (e.g., MLP). The proton 532 is further depicted as exiting the object 520 and being measured by a detector so as to yield an i-th value of the measurement vector b. In some implementations, an element $a_{ij}$ of the transformation matrix A can represent an interaction parameter such as an intersection length of the i-th proton with the j-th voxel of the object vector x.

In some implementations, the transformation matrix A can be configured in a number of ways so as to facilitate the estimations of the intersection lengths ($a_{ij}$s). For example, the most likely path (MLP) can be discretized in step sizes relative to the voxel size (e.g., sub-voxel step size such as half-voxel step).

In some implementations, the intersection length $a_{ij}$ can be estimated in a number of ways. For example, any voxel that intersects with the MLP can be assigned a constant value for the interaction length. In another example, the length of a chord of the MLP that intersects with a given voxel can be calculated and assigned to that voxel. In yet another example, a mean effective chord length factor can be multiplied to a constant value assigned to all of the voxels along the MLP; and such a factor can be based on the incidence angle of the proton on the object grid.

Figure 17:
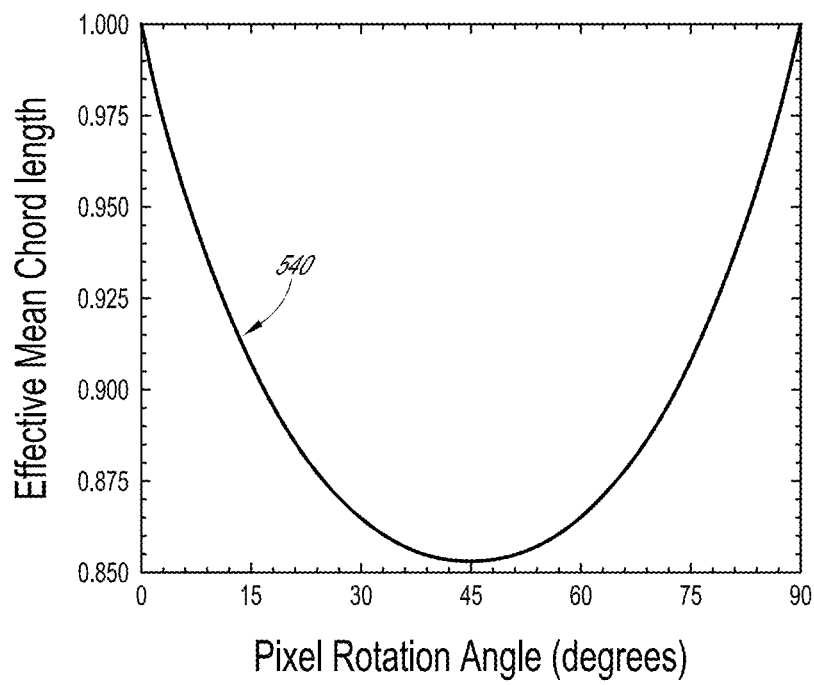
FIGS. 17 and 18 show an example of how intersections of proton paths with voxels of a target can be characterized for estimating a system matrix describing the discrete interaction approach of FIG. 15.
Figure 18:
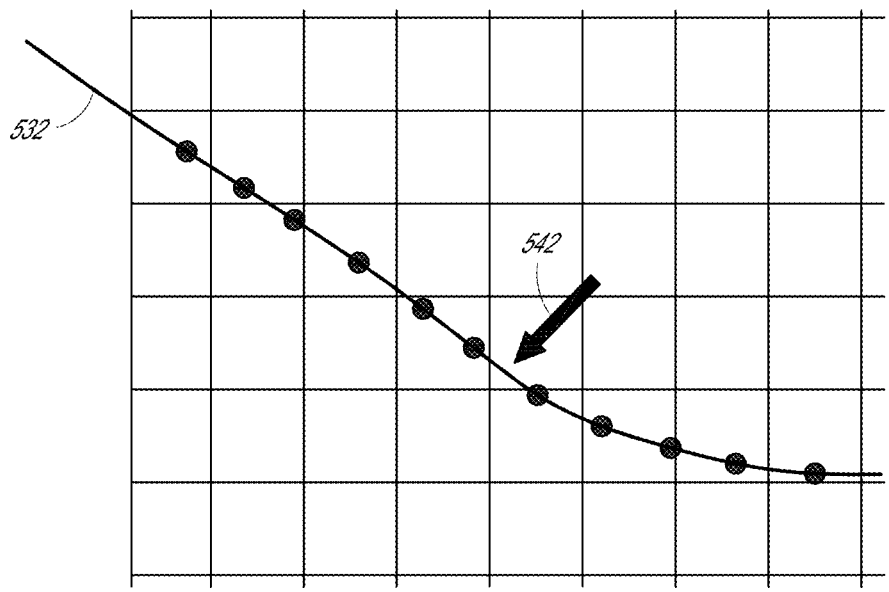

FIG. 17 shows an example plot 540 of the foregoing mean effective chord length factor, where the indicated incidence angle is relative to the object grid 520 (FIG. 18) oriented so that a horizontal incidence would have an incidence angle of zero. In such an example, a horizontal intersection is given a factor of 1, and a 45 degree intersection is given the smallest value. Such an assignment takes into account that an angled intersection is likely to be shorter (e.g., segment indicated by arrow 542) than a lateral dimension (e.g., horizontal dimension of a square voxel), even though the full diagonal length is longer. In some implementations, the foregoing adjustment based on a single parameter (incidence angle) can desirably reduce processing time.

Figure 19B:
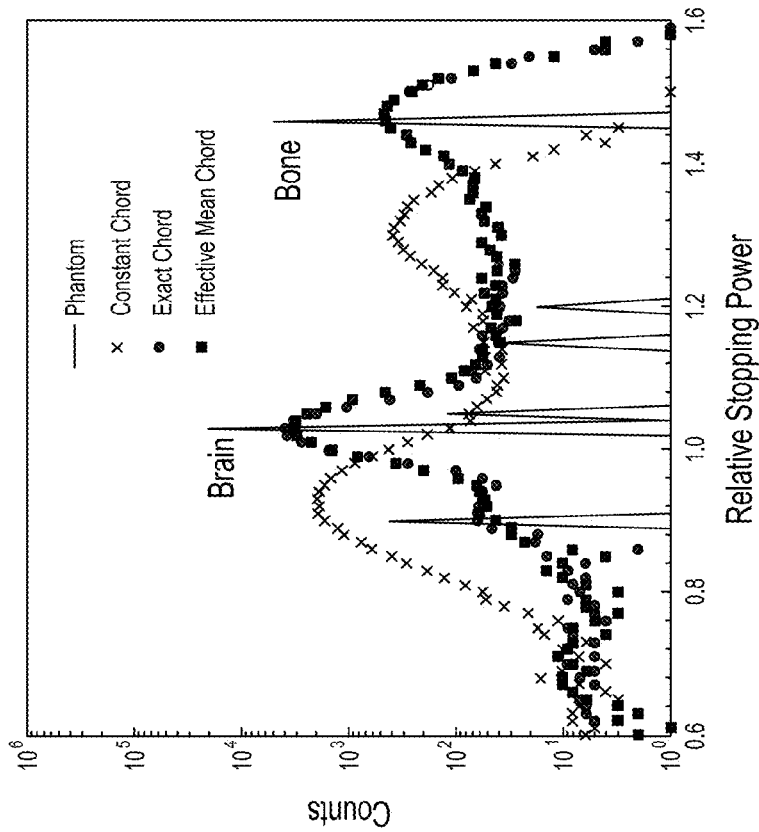
FIGS. 19A and 19B show example results of reconstructions of simulated data.
Figure 19A:
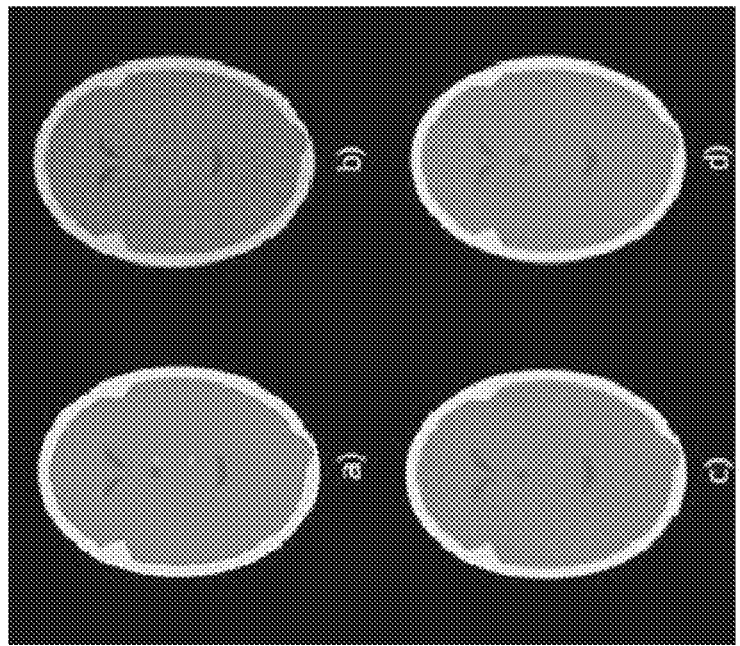

FIGS. 19A and 19B show examples of image quality and stopping power characterization performance that can result from use of the foregoing intersection length estimations. In FIG. 19A, the upper left image is a reconstructed image of a phantom resulting from Monte Carlo simulation using a 2-dimensional proton beam. The upper right image is a reconstructed image of the phantom using the constant interaction length approach. The lower left is for the effective mean chord length factor approach, and the lower right is for the voxel-by-voxel calculated chord length approach.

The image resulting from the constant interaction length approach is shown to be relatively noisier than the images obtained using the effective mean chord length factor approach and the voxel-by-voxel calculated chord length approach. Aside from the image quality, and as shown in FIG. 19B, the effective mean chord length factor approach and the voxel-by-voxel calculated chord length approach result in more accurate reproductions of relative stopping powers of the various features in the phantom than that of the constant interaction length approach.

In some implementations, the system of linear equations (e.g., A·x=b) described herein in reference to FIGS. 15 and 16 can be represented as follows. The vector b can represent a measurement (e.g., energy loss) vector for m protons, such that b has m elements $b_i$ with i=1 to m. The vector x can be an unknown image vector having values of a parameter (e.g., relative stopping power, RSP) of the object being characterized. Thus, in the context of an i-th proton traversing the object along its MLP and resulting in a measured energy loss, the i-th element, $b_i$, of the vector b represents the integrated RSP along the MLP. Such a quantity can be measured, for example, by calibrating the energy detector response to protons that traversed a block of material of known thickness and relative stopping power, or calculated numerically by the left side of Equation 1, such that $$b_i = \int_{E_{out}}^{E_{in}} \frac{dE}{S_{water}(E)} \quad (2)$$

where $S_{water}$ represents proton stopping power in water given by $$S_{water} = \frac{4\pi r_e^2 m_e c^2 \eta_{water}}{\beta^2(E)} \left[ \ln\left(\frac{2m_e c^2}{I_{water}} \frac{\beta^2(E)}{1-\beta^2(E)}\right) - \beta^2(E) \right]. \quad (3)$$

In Equation 3, $r_e$ is the classical electron radius, $m_e$ the electron mass, $\eta_{water}$ and $I_{water}$ the electron density and mean ionization potential of water, respectively, and $\beta$ the velocity of the proton relative to the speed of light c.

In some implementations, the image vector x can be solved or estimated by utilizing an iterative reconstruction technique. For the purpose of description, suppose that a set I has m indices, so that I={1, 2, . . . , m}, and let a set {$H_i$: i an element of I} be a finite family of hyperplanes in n-dimensional real coordinate space $R^n$. The sets $H_i$, on which the vectors $x^k$ are projected during an iterative process, can be defined by the i-th row of the m×n linear system Ax=b, such that $$H_i = \{x \in R^n \langle a^i, x \rangle = b_i\}, \text{ for } i=1,2,\ldots,m. \quad (4)$$

In Equation 4, $a^i$ is the i-th column vector of $A^T$ (the transpose of A), such that its components occupy the i-th row of A.

In some implementations, an object function $S_i$ satisfying the i-th hyperplane $H_i$ of Equation 4 can be represented as a set of x (element(s) of $R^n$), with a constraint where a cost or merit function $$g_i(x) = |\langle a_i, x \rangle - b_i| - \varepsilon_i \quad (5)$$

is less than or equal to zero, and where $\varepsilon_i$ is a threshold parameter defining the half-width of a hyperslab. An overall object function S can then be determined as an intersection of m $S_i$ functions, such that $S = \cap S_i$, with i=1 to m.

Figure 20A:
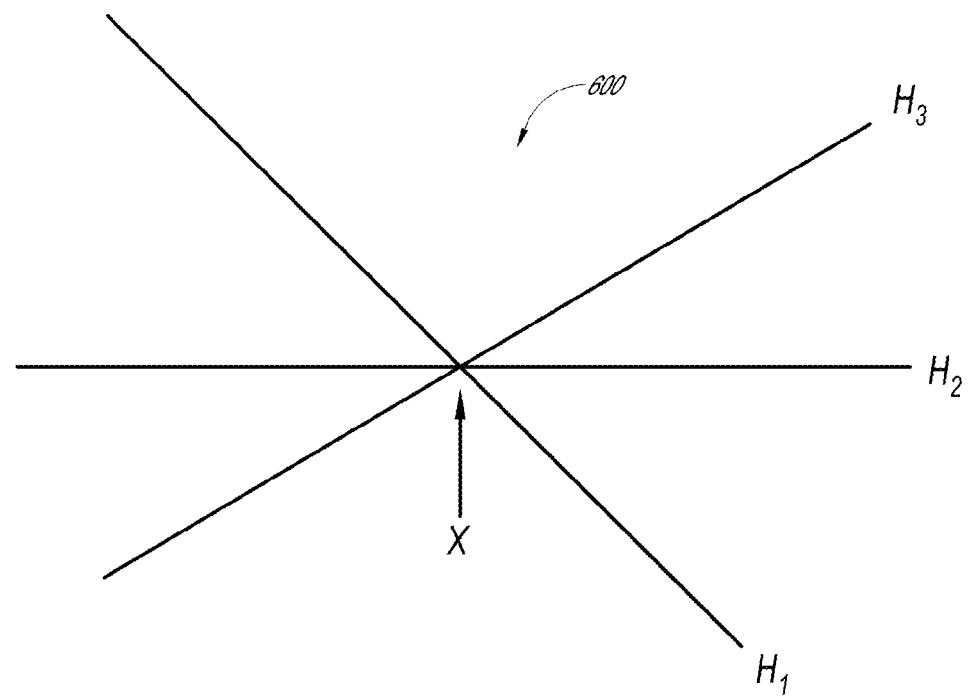
FIG. 20A depicts a number of hyperplanes for an ideal reconstruction situation where proton energy measurements are substantially noise-free and MLPs are substantially exact, where each hyperplane represents an equation in a system of linear equations that characterizes a transformation of an object function of the target to projections by a system matrix representative of interaction of protons in discrete voxels of the target, such that substantially all hyperplanes intersect at a point representative of a true object function.

In an ideal situation where proton energy measurements are substantially noise-free and the MLPs are substantially exact, such an object function S can be represented as a single point where all of the hyperplanes intersect. Such an ideal situation is depicted in FIG. 20A, where example hyperplanes 600 are shown to intersect at a point indicated as "X." In such an ideal situation, the threshold parameter $\varepsilon_i$ can be substantially zero, and a substantially exact solution can be obtained where $\langle a_i, x \rangle = b_i$ ($g_i(x)=0$).

In a more realistic situation, proton energy measurements are not noise-free, and MLPs are not exact. In such a situation, a hyperplane can be depicted as a slab instead of a plane, such that intersections of such hyperslabs can result in a region where all of the hyperslabs overlap. Such a situation is depicted in FIG. 20B, where example hyperslabs 610 are shown to intersect at a region indicated as "Q." In such a situation, the threshold parameter $\varepsilon_i$ can be a quantity greater than zero and defining an outer bound of permissible solutions that satisfy the merit function of Equation 5.

Figure 20B:
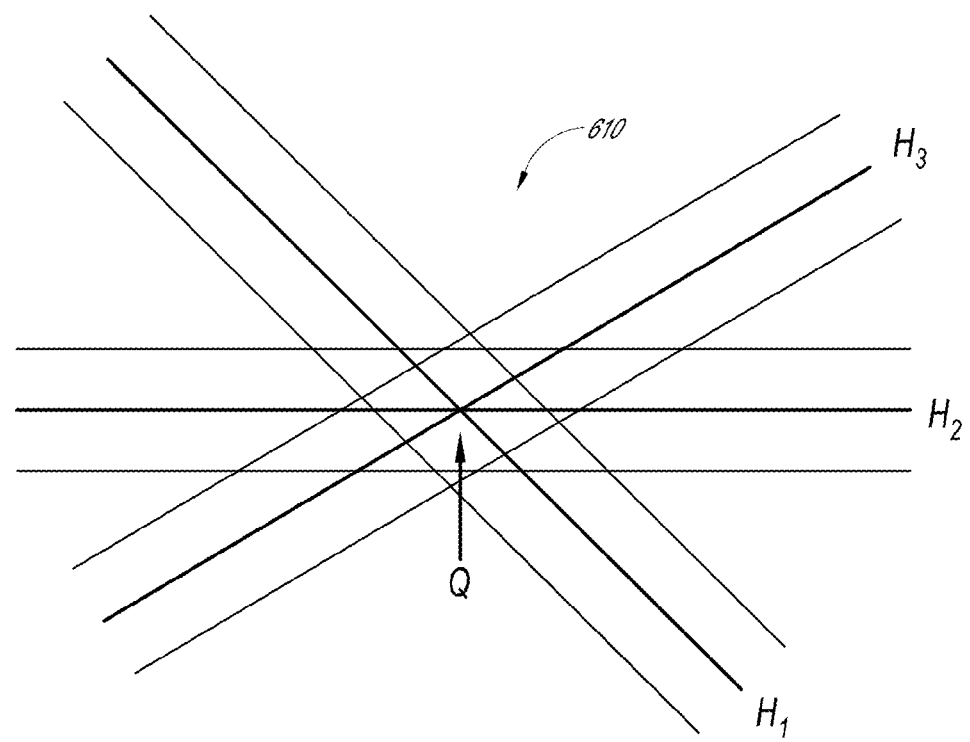
FIG. 20B depicts a number of hyperslabs for a more realistic reconstruction situation where proton measurements are not noise-free and MLPs are not exact, such that the hyperslabs may intersect in a convex region containing a true object function.

In the example of FIG. 20B, a desired object function S that characterizes the medium being imaged can be within the overlap region Q. More generally, a desired object function S that characterizes the medium being imaged can be within the constrained space $\varepsilon = \{\varepsilon_i\}$.

In some implementations, such a desired object function can be obtained by an optimization technique such as minimization. While optimization can have certain advantages in some imaging applications, it could also have drawbacks. For example, an optimal solution, as dictated by a merit function, may not always be a solution that best reproduces the true object data of interest. Such an effect can result from, for example, inconsistencies in the acquired data and/or due to the choice of merit function. Further, such a choice of merit function can be affected by arguments that are sometimes inadequate and/or by the ability or inability to computationally handle the resulting optimization problem. In some implementations, the optimization approach can also be impractical due to limitations in computational resources such as memory and processing power.

In some implementations, proton CT image reconstruction can be performed utilizing one or more of feasibility seeking methods. For an imaging situation that yields an intersection of a finite family of convex sets (e.g., the example intersection region Q resulting from a set of hyperslabs 610 in FIG. 20B), a plurality of solutions can exist. In a convex feasibility problem (CFP) methodology, a solution among such a number of solutions can be searched for and obtained; and such a solution can correspond to a point within the intersection region.

For image reconstructions (e.g., pCT reconstruction) based on the CFP methodology, desirable performance can be based on factors such as use of an efficient feasibility seeking projection method, and finding of a feasible solution having a reduced value of a given merit function. In some implementations, superiorization can refer to such a process of finding a superior solution with respect to some merit function, which is also a feasible solution of corresponding CFP sets. A superior solution can be a feasible solution of the CFP for which the value of the merit function, with respect to which one superiorizes, is smaller (but not necessarily minimal) than the value of this function at a feasible point that would have been reached if the superiorization process would not have been applied.

In some implementations, the foregoing projection method that provides an efficient feasibility seeking capability can be selected based on one or more factors that include bounded perturbation resilience. An ability to perturb a given projection algorithm without losing convergence to a feasible point can allow steering of the algorithm toward a feasible point that is superior, in the context of the merit function, than another feasible point that would be arrived at without the perturbations.

Without desiring or intending to be bound by any particular theory, an algorithm P can be said to be resilient to bounded perturbations if the following are satisfied. If a sequence $$((P)^k x)_{k=0}^\infty$$

(obtained by sequential repeated applications of P, starting from x) converges to a solution of problem Q for all x in the n-dimensional real coordinate space $R^n$, then any sequence $$(x^k)_{k=0}^\infty$$

of points in $R^n$ also converges to a solution of Q provided that for all k≥0, $$x^{k+1} = P_Q(x^k + \beta_k v^k), \quad (6)$$

where $\beta_k v^k$ are bounded perturbations, meaning that $\beta_k$ are real non-negative numbers such that $$\Sigma_{k=0}^\infty \beta_k < \infty$$

and the sequence of vectors $$(v^k)_{k=0}^\infty$$

is bounded.

In some implementations, the superiorization methodology can be utilized as follows. Instead of trying to solve a constrained minimization problem, the superiorization approach can perturb some feasibility seeking algorithms so that, without losing their convergence toward feasibility, they will yield a point (or points) with reduced objective function value(s). Thus, in some implementations, one or more feasibility seeking projection algorithms for pCT imaging can include or be adapted to include such a perturbation resilience property. Non-limiting examples of such perturbation resilient projection algorithms, or algorithms that can be adapted to include such a capability, are described herein in greater detail.

Figure 21B:
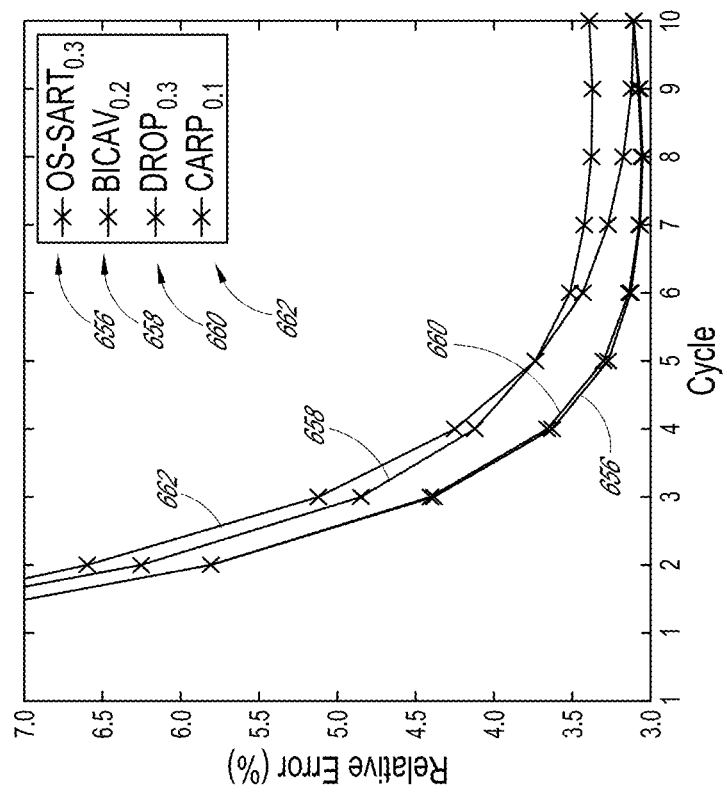
FIGS. 21A, 21B, 22 and 23 show example performance results for different projection techniques.
Figure 21A:
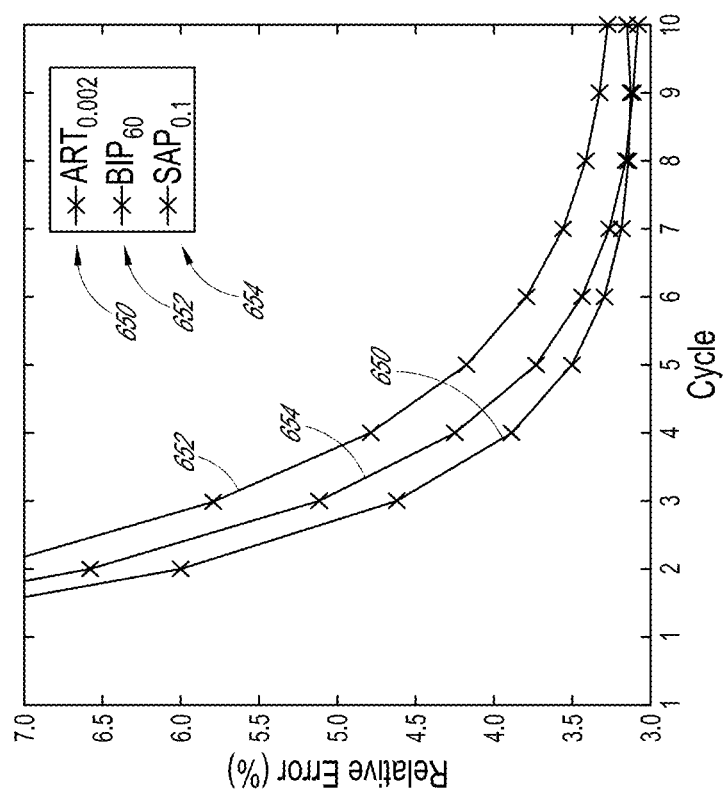
Figure 22:
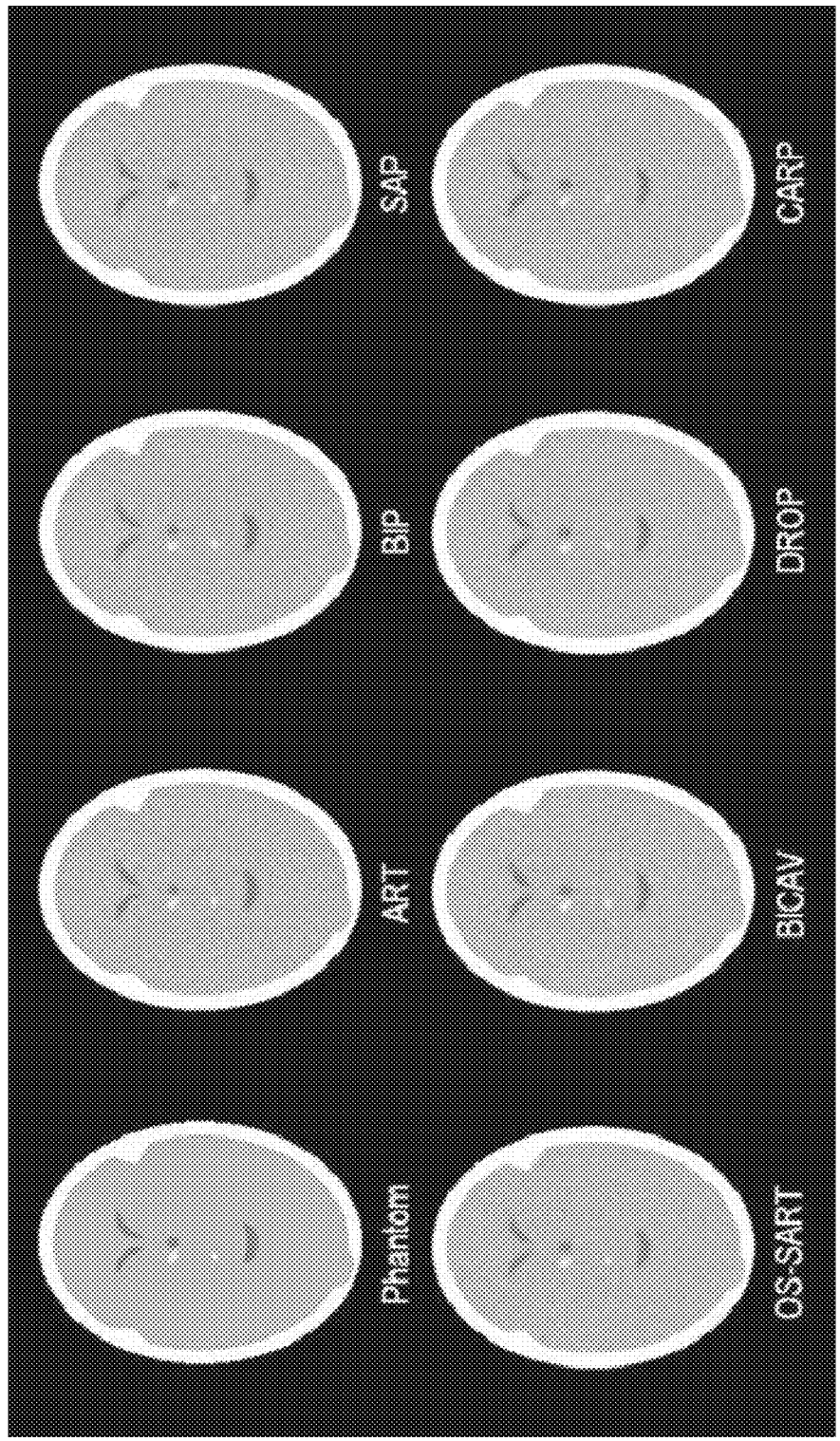
Figure 23:
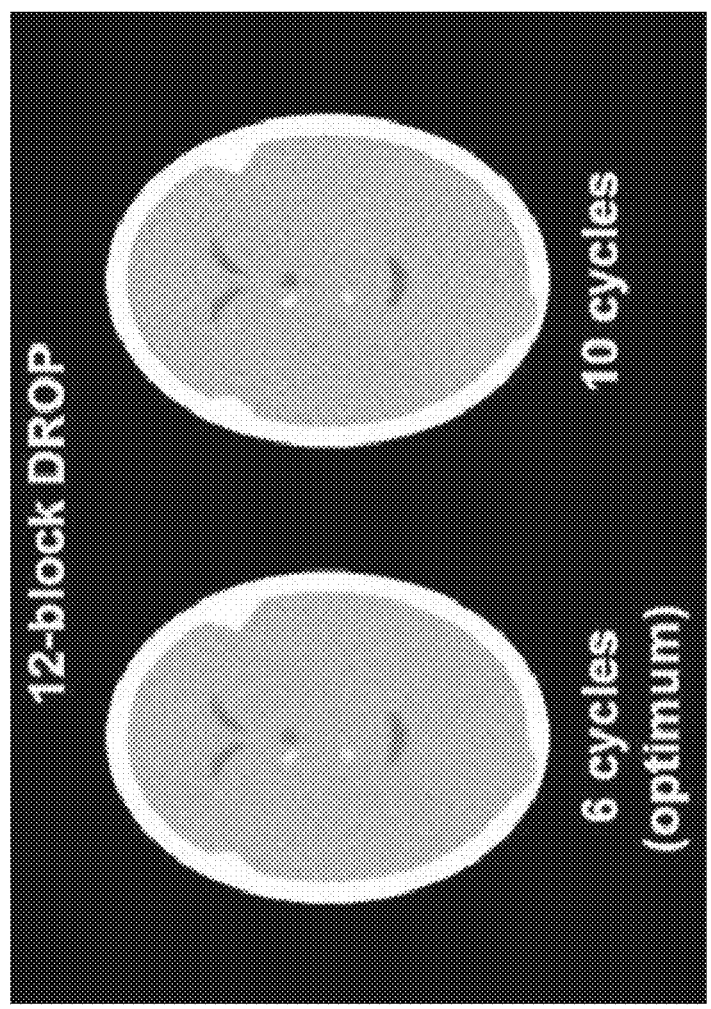

Applicant has analyzed a number of projection algorithms that can be utilized for the superiorization methodology; and some results of such analyses are described in reference to FIGS. 21-23. FIGS. 21A and 21B show performance curves (e.g., relative error as a function of number of iteration cycles) for reconstructions of simulated GEANT4 proton interactions using example projection algorithms ART (650), BIP (652), SAP (654), OSART (656), BICAV (658), DROP (660), and CARP (662). FIG. 22 shows an image of a phantom (upper row, first column) that was used in the simulation of the proton interactions, as well as reconstructed images using the foregoing projection algorithms. FIG. 23 shows a comparison of images obtained by different numbers of iterations of an example projection algorithm (DROP), showing that in some situations, additional iterations beyond some point do not necessarily increase the image quality significantly.

The example performance related plots and images of FIGS. 21-23 were obtained using a known optimization technique. Additional references to these example performance related illustrations are made in descriptions of the example projection algorithms.

In some implementations, a perturbation resilient projection algorithm can be a sequential projection algorithm such as ART (algebraic reconstruction technique) that is known to one of ordinary skill in the art. The ART algorithm, as applied to proton CT reconstruction, can be slow due to its sequential nature. Additional details concerning the ART algorithm can be found at, for example, G. T. Herman, Fundamentals of Computerized Tomography: Image Reconstruction from Projections, 2nd ed., Springer, New York, N.Y., 2009. In FIGS. 21A and 22, the ART projection algorithm as applied to the example GEANT 4 simulation is represented as a curve 650 and an image on the upper row, second column.

In some implementations, the ART algorithm can be modified as a simultaneous ART (SART) algorithm. In some implementations, an ART based algorithm, such as the SART algorithm, can be modified as a block-iterative algorithm (e.g., block-iterative SART, or OS-SART). The SART algorithm, as applied to proton CT reconstruction, can be configured to converge to a least-squares minimum. However, the algorithm can still be slow due to a relatively small weighting value of (1/m), where the quantity m represents the number of protons in the data set. In FIGS. 21B and 22, the OSART projection algorithm as applied to the example GEANT 4 simulation is represented as a curve 656 and an image on the lower row, first column.

In some implementations, a perturbation resilient projection algorithm can be a block-iterative projection (BIP) algorithm. Such an algorithm was developed by Aharoni and Censor; and additional details concerning the algorithm can be found at, for example, R. Aharoni and Y. Censor, "Block-iterative projection methods for parallel computation of solutions to convex feasibility problems," Linear Algebra and its Applications, 120, 165-175 (1989). In some implementations of the BIP algorithm, simultaneous projections can occur within each block of hyperplanes; and a number of such blocks of hyperplanes can be sequentially processed iteratively. In some implementations, the BIP algorithm can be configured so as to provide weighting according to block size(s), thereby avoiding the slow reconstruction problem associated with the 1/n weighting value. In FIGS. 21A and 22, the BIP projection algorithm as applied to the example GEANT 4 simulation is represented as a curve 652 and an image on the upper row, third column.

In some implementations, a perturbation resilient projection algorithm can be a string-averaging projection (SAP) algorithm. Such an algorithm was developed by Censor, Elfving and Herman; and additional details concerning the algorithm can be found at, for example, Y. Censor, T. Elfving, and G. T. Herman, "Averaging strings of sequential iterations for convex feasibility problems," Inherently Parallel Algorithms in Feasibility and Optimization and Their Applications, Elsevier Science Publications, Amsterdam, The Netherlands, D. Butnariu, Y. Censor, and S. Reich (Ed), 101-114 (2001). In some implementations of the SAP algorithm, a plurality of strings can be formed, each having a string of hyperplanes. Sequential projection can be performed within each string, and such sequential projections can be performed in parallel for the plurality of strings. Such projections can be processed as iterations of convex combinations of all of the strings. In FIGS. 21A and 22, the SAP projection algorithm as applied to the example GEANT 4 simulation is represented as a curve 654 and an image on the upper row, fourth column.

In some implementations, a perturbation resilient projection algorithm can be a component averaging (CAV) algorithm. Such an algorithm was developed by Censor, Gordon and Gordon; and additional details concerning the algorithm can be found at, for example, Y. Censor, D. Gordon, and R. Gordon, "Component averaging: An efficient iterative parallel algorithm for large and sparse unstructured problems," Parallel Computing, 27, 777-808 (2001). In some implementations, the CAV algorithm can be configured to be substantially fully simultaneous; and the 1/n weighting factor can be replaced by a family of diagonal matrices, with the diagonal elements equal to number of protons intersecting j-th voxel. Such a configuration can yield non-orthogonal projections. In some implementations, the CAV algorithm can be modified to operate as a block-iterative CAV (BICAV) algorithm. In some implementations, the CAV algorithm can be modified to operate as a component averaging row projection (CARP) algorithm. In FIGS. 21B and 22, the BICAV projection algorithm as applied to the example GEANT 4 simulation is represented as a curve 658 and an image on the lower row, second column. In FIGS. 21B and 22, the CARP projection algorithm as applied to the example GEANT 4 simulation is represented as a curve 662 and an image on the lower row, fourth column.

In some implementations, a perturbation resilient projection algorithm can be a diagonally relaxed orthogonal relaxation (DROP) algorithm. Such an algorithm was developed by Censor, Herman, Elfving and Nikazad; and additional details concerning the algorithm can be found at, for example, Y. Censor, T. Elfving, G. T. Herman, and T. Nikazad, "On diagonally-relaxed orthogonal projection methods," SIAM Journal of Scientific Computing, 30, 473-504 (2008). In some implementations, the DROP algorithm can be configured to be substantially fully simultaneous; and the weighting approach can be similar to that of the CAV algorithm. However, the resulting projections can be orthogonal. In some implementations, the DROP algorithm can be modified to operate as a block-iterative DROP (BIDROP) algorithm. In FIGS. 21B and 22, the DROP projection algorithm as applied to the example GEANT 4 simulation is represented as a curve 660 and an image on the lower row, third column.

In some implementations, a perturbation resilient projection algorithm can be a simultaneous algebraic reconstruction technique (SART) algorithm having a modified weighing scheme. Such an algorithm was developed by Anderson and Kak; and additional details concerning the algorithm can be found at, for example, A. H. Andersen and A. C. Kak, "Simultaneous algebraic reconstruction technique (SART): A superior implementation of the ART algorithm," Ultrasonic Imaging, 6, 81-94 (1984). In some implementations, such an algorithm can be configured to be substantially fully simultaneous; and the weighting can by a quantity of 1 over the sum of non-zero elements of each matrix row. In some implementations, such an algorithm can be modified to operate as a block-set-iterative (OSART) algorithm.

Other projection algorithms can also be utilized, with or without the example total variation superiorization methodologies described herein. Additional details concerning examples of such projection algorithms can be found in articles such as (i) D. Butnariu, Y. Censor and S. Reich (Editors), Inherently Parallel Algorithms in Feasibility and Optimization and Their Applications, Elsevier Science Publishers, Amsterdam, The Netherlands, 2001; (ii) Y. Censor and S. A. Zenios, Parallel Optimization: Theory, Algorithms, and Applications, Oxford University Press, New York, N.Y., USA, 1997; and (iii) Y. Censor, W. Chen, P. L. Combettes, R. Davidi and G. T. Herman, On the effectiveness of projection methods for convex feasibility problems with linear inequality constraints, Technical Report, Dec. 22, 2009, available on arXiv at: http://arxiv.org/abs/0912.4367.

As described herein, the superiorization approach can include a process of finding a superior solution with respect to some merit function, where such a superior solution is also a feasible solution of corresponding convex feasibility problem (CFP) sets, including a set resulting from perturbation resilient projections. In some implementations, such a merit function can include a total variation (TV) function, such that the superiorization can be a TV superiorization (TVS).

To demonstrate the total variation superiorization technique, Applicant used a block-iterative version of the DROP projection algorithm (BIDROP) as described herein. It will be understood that such a TVS technique can also be implemented with other projection algorithms, including those disclosed herein.

The example BIDROP algorithm can be used by partitioning the set of the hyperplane indices I as a union of M blocks such that $I = I_1 \cup I_2 \cup \ldots \cup I_M$. In some implementations, the M blocks can be fixed blocks. As described herein, the BIDROP algorithm can be considered to be a variant of a block-iterative projection method that employs a component-dependent weighting scheme.

In some implementations, the BIDROP can be configured as follows. An initialization can include selecting a value of a first element $x^0$ of the object vector x. Such a value of $x^0$ can be arbitrary or be estimated using, for example, a filtered backprojection (FBP) method.

In some implementations, an iterative step can include, for a given vector element $x^k$, computation of the next iterate $x^{k+1}$, with $$x^{k+1} = P_{t(k)}(x^k) = x^k + \lambda_k U_{t(k)} \sum_{i \in I_{t(k)}} \frac{b_i - \langle a^i, x^k \rangle}{\|a^i\|^2} a^i. \tag{7}$$

In Equation 7, the diagonal matrix $U_{t(k)}$ can be represented as $$U_{t(k)} = \text{diag}(\min(1, 1/h_j^t)),$$

with $h_j^t$ being the number of proton histories in the t-th block that intersects the j-th voxel, and $$(\lambda_k)_{k=0}^\infty$$

being a sequence of user-selected relaxation parameters. In the example demonstration of the TVS technique as described herein, $\lambda$ was kept at a value of approximately 1.9 based on the results with BIDROP and the data divided into 12 blocks, as shown in FIG. 23. Further, the blocks are taken up by the algorithm according to a control sequence $$t(k)_{k=0}^{28}$$

which is a cyclic control such that t(k)=k mod M+1. An example proton data set was partitioned into 12 blocks of substantially equal size and having substantially equal number of proton histories from each projection angle.

In some implementations, a merit function $\phi$ and/or a proximity function Pr can be selected to steer superiorization reconstruction. The feasibility proximity function can be selected to provide a residual of measured integral relative stopping power (RSP) values and those obtained with the current image estimate. Such a feasibility proximity checking can be utilized to ensure that superiorization with respect to an additional task represented by the merit function $\phi$ does not steer the solution away from an agreement with the measured data. In some implementations, the feasibility proximity of the current image estimate $x^k$ to the measured data can be calculated as $$Pr(x^k) = \sqrt{\sum_{i=1}^m \left(\frac{b_i - \langle a^i, x^k \rangle}{\|a^i\|}\right)^2}, \tag{8}$$

where m is the number of proton histories in a set of interest.

In some situations, a feasible set (of the intersection of the constraints) can be empty. Even in such situations, reducing the proximity function of Equation 8 can lead to a point which "violates" the constraints less; and thus can be useful even if the proximity function does not reach (and in some situation may not be able to reach) a value of zero.

In some implementations, the merit function $\phi$ to be reduced during the reconstruction process and associated with the total variation of the reconstructed image estimate can be represented as $$\phi(p^k) = \sum_{g=1}^{J-1} \sum_{l=1}^{J-1} \sqrt{(p_{g+1,l}^k - p_{g,l}^k)^2 + (p_{g,l+1}^k - p_{g,l}^k)^2}, \tag{9}$$

where $p^k$ is a two-dimensional $J \times J$ representation of the n-dimensional image vector $x^k$.

In some implementations, a perturbation vector v for steering the iterative sequence of image estimates towards reduced total variation of the image estimate can be calculated. For example, the perturbation vector can be calculated as the negative of a normalized subgradient of the total variation at $x^k$, such that $$v^k = \begin{cases} -\dfrac{s^k}{\|s^k\|}, & \text{if } s^k \neq 0, \\ 0, & \text{otherwise} \end{cases} \tag{10}$$

In some implementations, the example subgradient (s) of total variation can be calculated in a manner described in an article authored by P. L. Combettes and J. Luo, "An adaptive level set method for nondifferentiable constrained image recovery," IEEE Trans. Image Process, 11, 1295-1304 (2002). Additional details concerning the foregoing example perturbation vector can be found in, for example, an article authored by D. Butnariu, R. Davidi, G. T. Herman, and I. G. Kazantsev, "Stable convergence behavior under summable perturbations of a class of projection methods for convex feasibility and optimization problems," IEEE J. Sel. Top. Signal Process, 1, 540-547 (2007).

Example 1

The foregoing example DROP based superiorization technique can be implemented in a number of ways. In a first example, an initial image estimate for subsequent iterative procedure can be acquired by performing a filtered back-projection (FBP) reconstruction from the measured data. Such a FBP can be carried out by rebinning individual proton histories to substantially conform with a known sonogram grid. For the iterative procedure, the DROP projection operator can be applied cyclically until all blocks of the data set is processed. In some implementations, an optional feasibility proximity calculation as described herein can be checked including substantially all histories in the data set.

In some implementations, the foregoing first example DROP based total variation superiorization technique can be coded in a number of ways. For example, such a coding can include an algorithm such as:

(1) set k=0
(2) set $x^k = x_{FBP}$ an initial FBP reconstruction, and $\beta_k = 1$
(3) repeat for N cycles
(4)   set s to a subgradient of $\phi$ at $x^k$
(5)   if $||s|| > 0$ set $v^k = -s/||s||$
(6)   else set $v^k = s$
(7)   set continue = true
(8)   while continue
(9)     set $y^k = x^k + \beta_k v^k$
(10)    calculate the merit function (total variation) with Equation 9, and if $\phi(y^k) \leq \phi(x^k)$
(11)      apply sequentially M times the projection operator $P_{t(k)}$ to $y^k$ (Equation 7)
(12)      calculate the feasibility proximity with Equation 8 using histories from all M blocks, and if $Pr(P_M y) < Pr(x^k)$
(13)        set $x^{k+1} = P_M y$
(14)        set continue = false
(15)      else set $\beta_k = \beta_k/2$
(16)    else set $\beta_k = \beta_k/2$
(17)  set k = k + 1

In some implementations, the quantity N representative of the number of cycles can be set at, for example, 10. Other values of N can also be used.

Example 2

In a second example, the DROP projection operator can be applied to a given block before continuing to an optional feasibility proximity check that is performed with histories from the subsequent block. Such an approach can be utilized when each block includes a substantially equal number of histories from each projection angle and thus can represent the data as a whole. Similar to the first example, an initial image estimate can be acquired by performing a filtered backprojection (FBP) reconstruction from the measured data.

In some implementations, the foregoing second example DROP based total variation superiorization technique can be coded in a number of ways. For example, such a coding can include an algorithm such as:

(1) set k=0
(2) set $x^k = x_{FBP}$ an initial FBP reconstruction, and $\beta_k = 1$
(3) repeat for each block over N cycles
(4)   set s to a subgradient of $\phi$ at $x^k$
(5)   if $||s|| > 0$ set $v^k = -s/||s||$
(6)   else set $v^k = s$
(7)   set continue = true
(8)   while continue
(9)     set $y^k = x^k + \beta_k v^k$
(10)    calculate the merit function (total variation) with Equation 9, and if $\phi(y^k) \leq \phi(x^k)$
(11)      apply the projection operator $P_{t(k)}$ to y (Equation 7)
(12)      calculate the feasibility proximity with Equation 8 using histories from the subsequent block, and if $Pr(P_{t(k)} y) < Pr(x^k)$
(13)        set $x^{k+1} = P_{t(k)} y$
(14)        set continue = false
(15)      else set $\beta_k = \beta_k/2$
(16)    else set $\beta_k = \beta_k/2$
(17)  set k = k + 1

In some implementations, the quantity N representative of the number of cycles can be set at, for example, 10. Other values of N can also be used.

Example 3

In a third example, the first example method can be modified such that the feasibility proximity check of step 12 is not performed. Such a modification may be desirable if a given feasibility proximity check is computationally demanding.

Example 4

In a fourth example, the second example method can be modified such that the feasibility proximity check of step 12 is not performed. Such a modification may be desirable if a given feasibility proximity check is computationally demanding.

Example 5

In a fifth example, a total variation (TV) function, including but not limited to Equation 9, can be utilized. In some implementations, the fifth example, which can be based on the DROP projection technique, can be coded in a number of ways. For example, such a coding can include an initialization can occur, where $x^0$=a selected value, and $\beta_0=1$. For an iterative step where $x^k$ and $\beta_k$ are given, $x^{k+1}$ and $\beta_{k+1}$ can be generated as follows:

(1) loop through a block index t
(2) calculate perturbation vector $v^k$
(3) set $z^k = x^k + \beta_k v^k$
(4) if $TV(z^k) > TV(x^k)$, set $\beta_k = \beta_k/2$ and go to (2), else proceed to (5)
(5) calculate the projection of $z^k$ onto hyperplanes within the current block with a DROP algorithm similar to Equation 7
(6) if $Res(y^k) > Res(x^k)$, set $\beta_k = \beta_k/2$ and go to (2), else proceed to (7)
(7) set $x^{k+1} = y^k$ and repeat (1) to (6) until a stopping condition applies.

In some imaging situations, it is possible to obtain a high quality image of an object at the expense of computing resources (e.g., computing power and time). It is generally desirable to obtain an image having a sufficient quality for intended use, and using acceptable amounts of resources. It is believed that one or more features of the present disclosure can provide such desirable quality and/or performance advantages when applied to proton CT applications.

Figure 24:
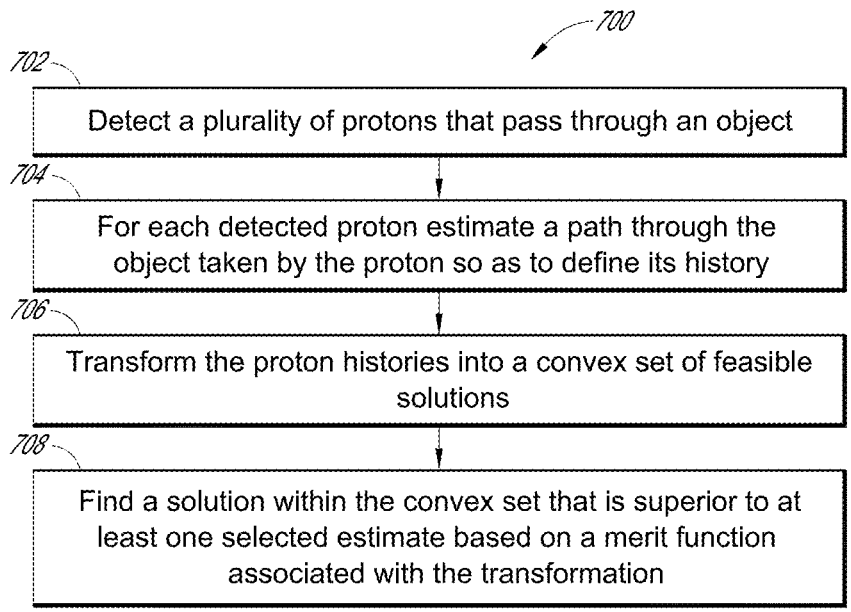
FIG. 24 shows a process that can be implemented to obtain a proton CT projection solution utilizing a superiorization methodology.

FIG. 24 shows that in some implementations, a process 700 can be performed so as to find a solution that allows formation of a proton CT image having a desired quality and/or a reconstruction performance feature. In block 702, a plurality of protons that have passed through an object can be detected. Examples of such proton detections (e.g., tracking and energy loss measurement) are described herein. In block 704, a path taken by each proton through the object can be estimated so as to characterize the proton's interaction in the object. Examples of such path estimations are described herein. In block 706, the protons' interaction histories can be transformed into a convex set of feasible solutions. Examples of such a transformation are described herein. In block 708, a solution that is within the convex set can be found based on a merit function associated with the transformation, where the solution is superior to at least one selected estimate or an existing solution. Examples of such a superiorization methodology are described herein.

Figure 25:
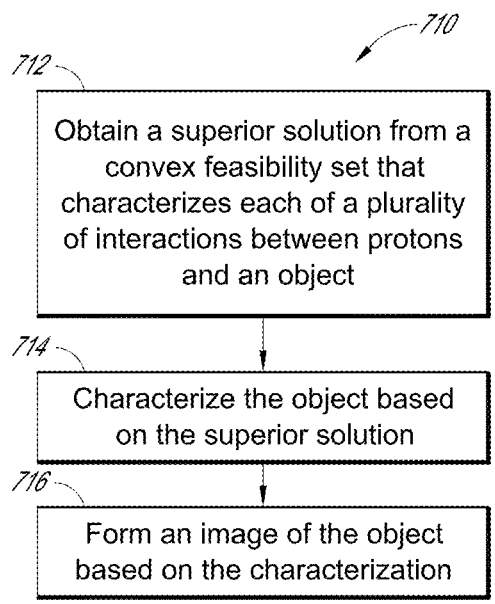
FIG. 25 shows a process that can be implemented to use a superior proton CT solution to characterize a target object.

FIG. 25 shows that in some implementations, a process 710 can be performed so as to yield an image based on a superior solution obtained via, for example, process 700 of FIG. 24. In block 712, a superior solution from a convex feasibility set can be obtained, where the convex feasibility set characterizes interactions of each of a plurality of protons with an object being imaged. In block 714, the object can be characterized based on the superior solution obtained in block 712. For example, a vector having desired voxel values can be calculated from the superior solution. In block 716, an image of the object can be formed based on the characterization of the object.

Figure 26A:
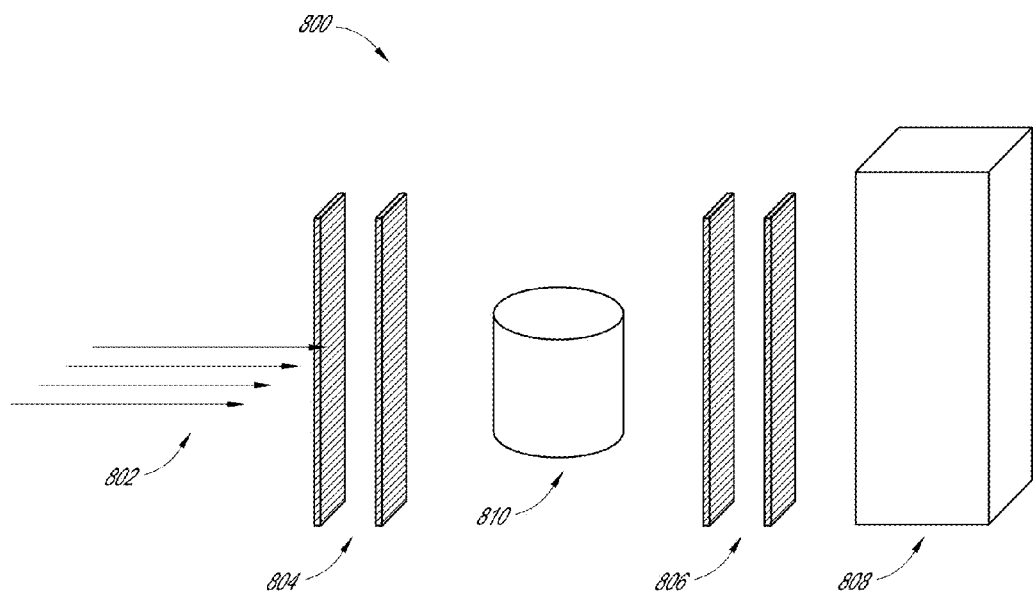
FIGS. 26A and 26B show an example proton CT configuration for simulating proton data to study various reconstruction schemes, including the superiorization methodology.
Figure 26B:
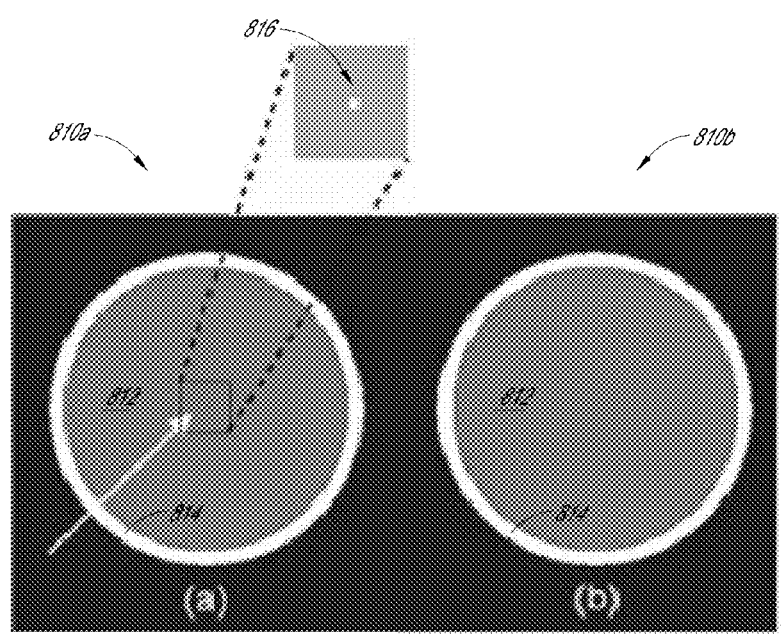
Figure 27:
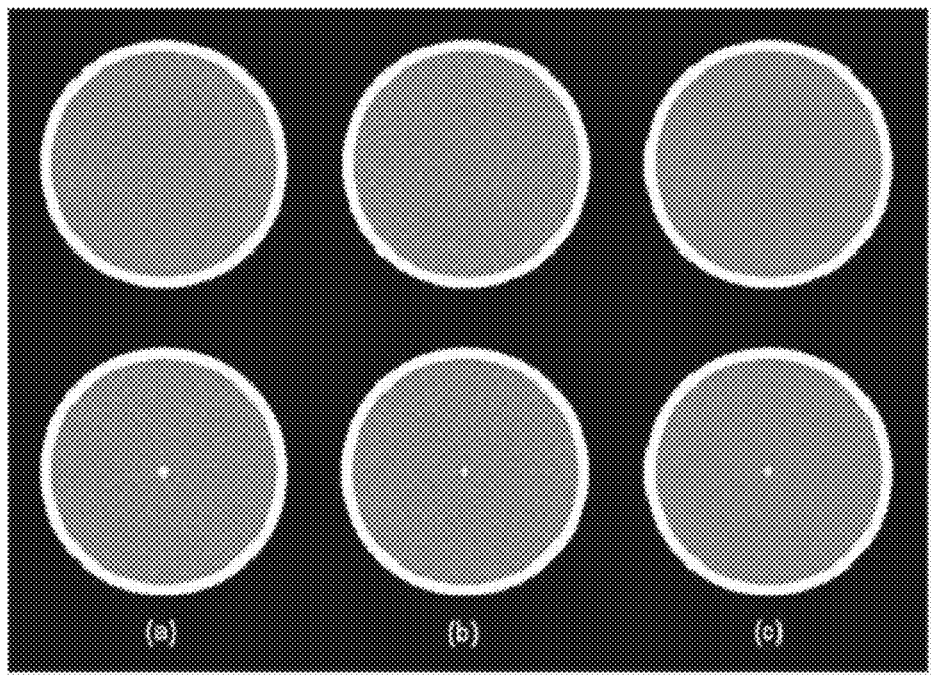
FIGS. 27-29 show example results of various reconstruction schemes based on simulated proton data.
Figure 28A:
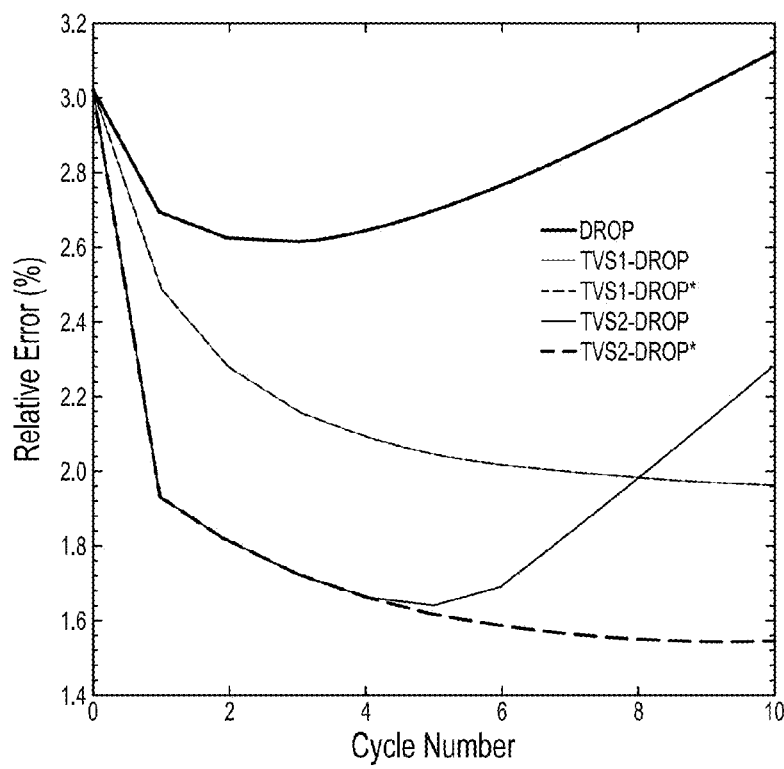
Figure 28B:
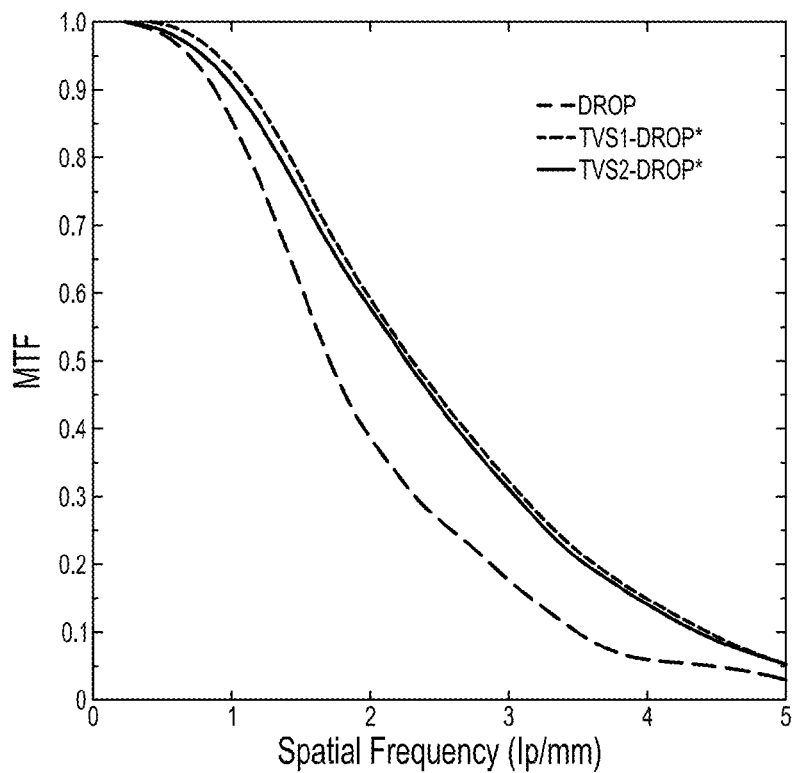
Figure 28C:
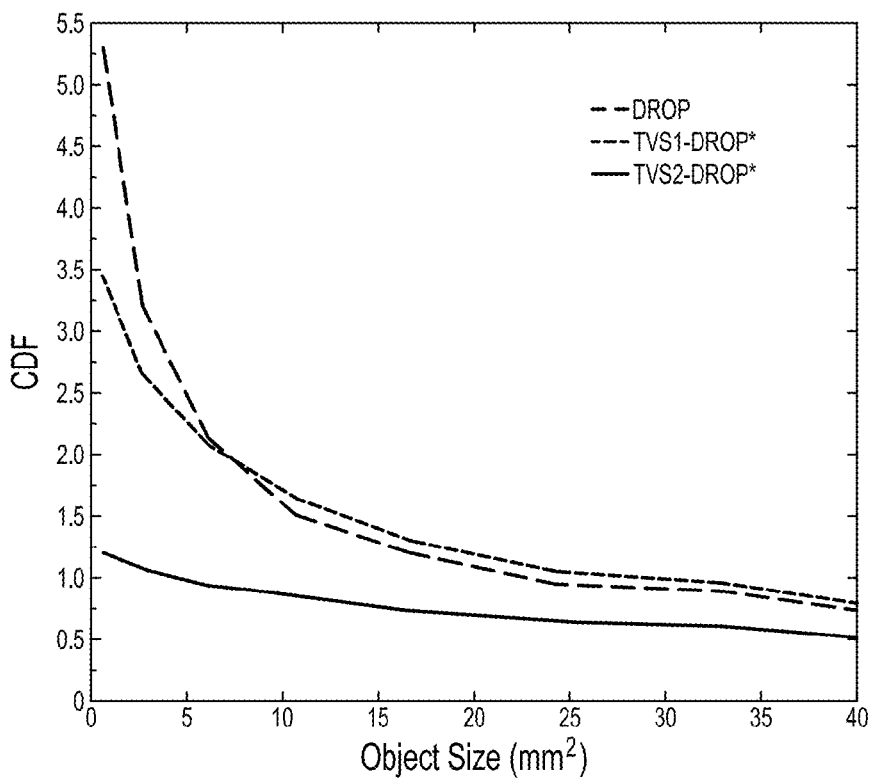
Figure 29:
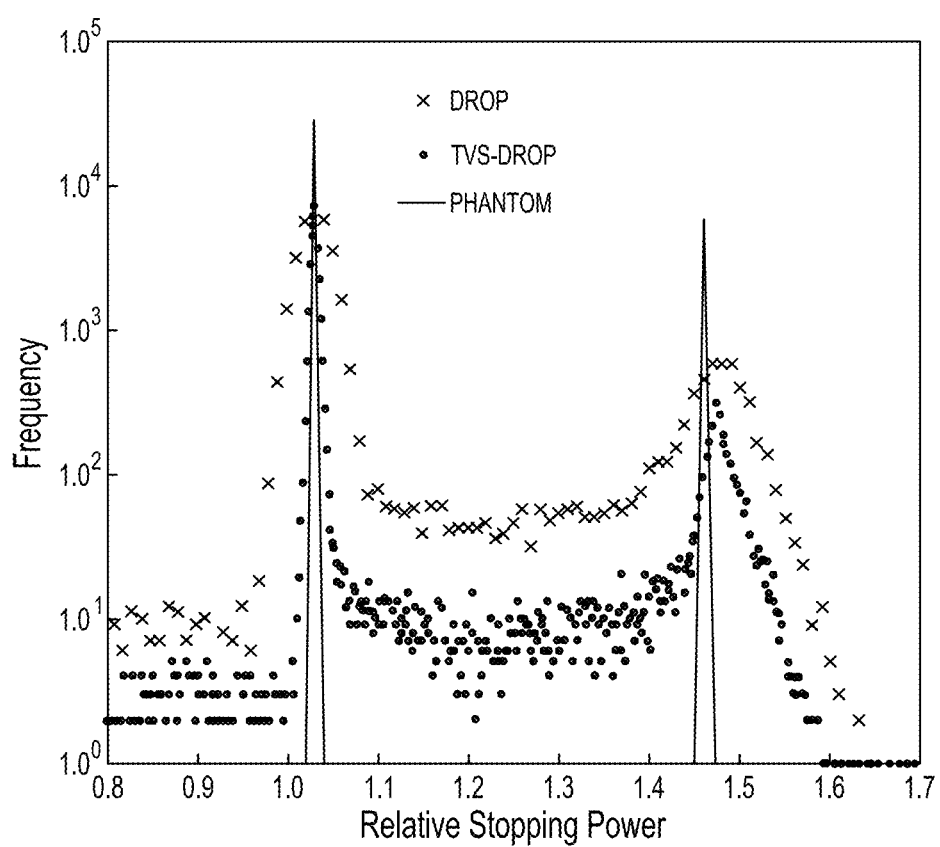

FIGS. 26A and 26B show an example proton interaction configuration 800 that was simulated via GEANT4; and FIGS. 27-29 show example results obtained from reconstruction methodologies described herein.

In the example simulation configuration 800, a detector system includes upstream tracking detectors (804) and downstream tracking detectors (806). Each of the upstream and downstream detectors 804, 806 includes two tracking planes so as to allow determination of incident and exit locations and directions of individual protons. Each tracking plane is configured as a 2D sensitive silicon tracking plane having dimensions of approximately 30 cm×30 cm, a thickness of about 0.04 cm, and an assigned spatial resolution of about 100 μm.

The detector system of the simulation configuration 800 further includes a CsI crystal calorimeter 808 having lateral dimensions of about 32 cm×32 cm and a thickness of about 10 cm. For simulating the response of the calorimeter 808, sources of detector noise were neglected, and the detector was configured as having a perfect energy resolution.

In the example simulation configuration 800, two different virtual phantoms (810) were used to quantify spatial and relative stopping power resolutions. Both phantoms, whose sectional views are shown in FIG. 26B, have a diameter of about 16 cm. Each phantom includes two materials, substantially equivalent in chemical composition and electron density to brain (812) and cranial bone (814) as defined by the International Commission on Radiological Protection (ICRP).

In FIG. 26B, the first example phantom 810a includes a central rectangular prism structure 816 having a cross-section of about (0.82×0.82) mm², approximately equal to a selected reconstruction voxel dimension. Such a phantom can allow estimation of spatial resolution of a given reconstruction methodology. The second example phantom 810b does not include such a central structure. For the example simulation, the electron density of the central structure 816 was selected to be about 20 times greater than the electron density of the surrounding brain material but retained the same chemical composition.

As shown in FIG. 26A, substantially monoenergetic protons having an energy of approximately 200 MeV formed a 2D parallel-beam geometry. One hundred eighty projections with about 2 degree intervals were simulated for each phantom. For each projection angle, positions on the tracking planes and energies deposited in the calorimeter were recorded for 20,000 protons.

To simulate the interactions of the protons with the phantoms, a GEANT4 hadronic ionization model was used. The model employs the Bethe-Bloch relationship for proton energies above 2 MeV, which covered an energy range of interest for protons traversing the phantom. For ionizing energy loss, a GEANT4 configuration includes calculation of a mean value in 100 steps evenly spaced logarithmically in kinetic energies from 1 keV to 100 TeV. However, studies have shown that such a default configuration may not be accurate enough for proton CT applications. Accordingly, the energy binning was calculated from 1 keV to 500 MeV in 2,000 steps. Low energy elastic and inelastic nuclear collision models in GEANT4 were enabled.

Based on the simulated proton data (including entry and exit coordinates and energy deposited in the calorimeter), a 2D image of each phantom was reconstructed with various DROP-based projection algorithms, and with and without the superiorization methodology. To perform parallel execution of calculations such as projections within a given block (e.g., the sum, in Equation 7, that can be independent from other blocks), GPGPUs (general purpose graphical processing units) were used. Following the completion of a block projection on a given GPGPU, the summed array was returned to a processor (e.g., a CPU) for further processing. The CPU also performed the sequential portion of the block-iterative algorithm.

Images obtained in the foregoing manner were further analyzed as follows. Spatial resolution of the reconstructed images was quantified with a 2D modulation transfer function (MTF) which can provide a measure of the signal transmission properties of an imaging system as a function of spatial frequency. For such a measure, a point spread function (PSF) of the image of the central dense rectangular prism (816 in FIG. 26B) was used. Following reconstruction, a 2D fast Fourier transform (FFT) of a 16×16 2D voxel region of interest centered on the PSF was carried out. Making use of the axial symmetry of the phantom, the MTF was obtained in the region of interest by averaging the magnitude of the x and y axial components of the resulting spatial frequency representation of the image.

Low-contrast density resolution was assessed with a contrast discrimination function (CDF) that can provide an objective statistical analysis method for determining a minimum contrast needed to discriminate an object of a given size from the surrounding tissue. The CDF was calculated by dividing the reconstructed image of the uniform phantom (810b in FIG. 26B) into a grid of objects, ranging from 1×1 to 10×10 2D voxels in size. A standard deviation of the distribution of mean pixel values within the grid elements were used to determine a minimum contrast detectable with a given confidence level. For a 95% confidence level, the detectable density difference between the object of selected grid size and the background was defined as 3.29 standard deviations of the mean pixel value distribution.

Quantitative accuracy of reconstructed relative stopping power (RSP) values was determined using histogram analysis and defining a relative RSP error as $$\varepsilon_n = \sum_j |x'_j - x''_j| \bigg/ \sum_j |x'_j|, \quad (11)$$

where $x'_j$ is the RSP in voxel j of the phantom, and $x_j^n$ is the reconstructed RSP in voxel j after n cycles.

FIG. 27 shows images reconstructed with (a) DROP without total variation superiorization, (b) DROP with TVS, but without the feasibility proximity checking in the first example (also described as the third example) (TVS1-DROP*), and (c) DROP with TVS, but without the feasibility proximity checking in the second example (also described as the fourth example) (TVS2-DROP*). Images in the top row are reconstructions of the uniform phantom (810b in FIG. 26B), and images in the bottom row are reconstructions of the spatial resolution phantom (810a in FIG. 26A). The example images result from an RSP window cut to include RSP values between 0.8 and 1.2.

In various example results shown in FIGS. 28A-28C, the DROP based TVS methodologies with the feasibility proximity checking are denoted by absence of the "*" symbol.

Images reconstructed with the foregoing methodologies and without the feasibility proximity checking had a smaller or approximately equivalent minimum relative error when compared to images reconstructed with the feasibility proximity check. Such effects are shown in FIG. 28A. All of the DROP-based TVS methodologies, with or without the feasibility proximity check, have less relative errors than the DROP-without-TVS methodology for iteration cycle number ranges that extend to at least 10. It should be noted that the images shown in FIG. 27 correspond to those obtained at their respective cycle of minimum relative error which was cycle 3 for DROP-without-TVS, and cycle 10 for TVS1-DROP* and TVS2-DROP*. Qualitatively, it can be seen that the TVS2-DROP* scheme had the lowest noise level, possibly due to the extra perturbation steps.

FIG. 28A shows plots of relative error as a function of cycle number for the various schemes. In the plots, the relative error at cycle 0 corresponds to the relative error produced by the FBP algorithm which was used to generate the initial point for the iterative TV superiorization.

The images reconstructed with the TVS1-DROP and TVS1-DROP* schemes (with and without the feasibility proximity check) are generally equivalent in terms of quantitative relative stopping power (RSP) accuracy and the relative error follows a monotonically decreasing trend as the cycle number increases. The removal of the feasibility proximity check does not make a significant difference as the check condition is not violated in this case.

On the other hand, the removal of the feasibility proximity check makes a significant difference for the TVS2-DROP scheme. FIG. 28A demonstrates that including the feasibility proximity check can lead to a progressive increase of the relative error after reaching a minimum similar to the DROP algorithm. Such an effect can be explained by the fact that the reduced β can dampen the noise-reducing effect of the perturbation step. Thus, as the DROP algorithm diverges from a low relative error, so does the more stringent TVS approach. This occurs with TVS2-DROP but not TVS1-DROP because violations of the feasibility proximity condition are observed with the former, but not the latter. Without the feasibility proximity check, the relative error of the TVS2-DROP* scheme follows a monotonically decreasing trend within the ten cycles. The minimum relative error within the first ten cycles is about 2.64% with DROP, about 1.96% with TVS1-DROP and TVS1-DROP*, about 1.64% with TVS2-DROP, and about 1.55% with TVS2-DROP*. These differences can result from various degrees of noise in the images reconstructed with the different schemes.

The foregoing example results were obtained with the data subdivided into 12 blocks. Another set of results were obtained with data subdivided into 180 blocks; and the results (not shown) were very similar to the 12-block results. Thus, in some implementations, block-iterative reconstruction algorithms processed with total variation superiorization methodology can be substantially insensitive to some changes in a number of blocks.

Histograms of the images presented in the top row of FIG. 27 were created to analyze the mean reconstructed value of the brain and bone-equivalent regions. Gaussian distributions were fitted to the peaks to model reconstruction noise. All schemes reconstructed substantially the same mean RSP value for the brain and bone-equivalent regions, within peak-fitting uncertainty. Thus, the TVS perturbation schemes did not adversely affect the accuracy of the reconstructed values of these materials.

Further analysis using the TVS1-DROP* and TVS2-DROP* schemes (both having improved noise performance and reduced reconstruction time) yielded MTF plots shown in FIG. 28B. For any spatial frequency in the plots, the TVS1-DROP* scheme has larger MTF values and thus superior spatial resolution than that of the DROP scheme. The TVS1-DROP* and the TVS2-DROP* schemes perform similarly in terms of spatial resolution, with the TVS1-DROP* scheme being marginally better. The improved spatial resolution with the TVS reconstruction schemes can be attributed to the greater number of cycles being performed before reaching the lowest relative error. It has been observed previously that pCT spatial resolution improves with cycle number when employing an MLP formalism in conjunction with an iterative algorithm. This can be an important result since some reconstruction methodologies that improve density resolution (described herein in reference to FIG. 28C) often display inferior spatial resolution.

The CDFs associated with the DROP and the reduced TVS-DROP* schemes are plotted in FIG. 28C. While the TVS1-DROP* scheme performs only slightly better than the DROP scheme, the TVS2-DROP* scheme performs much better than the other two schemes. For objects as small as about 1 $mm^2$, the TVS2-DROP* scheme allows contrast discrimination between about 1% and 1.5%. The superior contrast discrimination of the TVS2-DROP* scheme can be attributed to the combination of reduced image noise and improved spatial resolution.

FIG. 29 shows that in some implementations, a superiorization scheme such as a total variation superiorization methodology can also yield an improved measurement of relative stopping power (RSP). An example plot in FIG. 29 shows sharp known stopping power peaks associated with a phantom (solid line), as well as those resulting from reconstruction of simulated data using the DROP methodology ("x" marks) and the TVS-DROP methodology (solid filled marks) (e.g., the fifth example described herein). The RSP distribution for the DROP example has a similar performance as the best of the examples described in reference to FIG. 19B (e.g., the effective mean chord length technique).

By implementing the TVS technique to such the DROP reconstruction method, the resulting distribution of the RSP is shown to replicate the actual RSP distribution significantly better.

Figure 30:
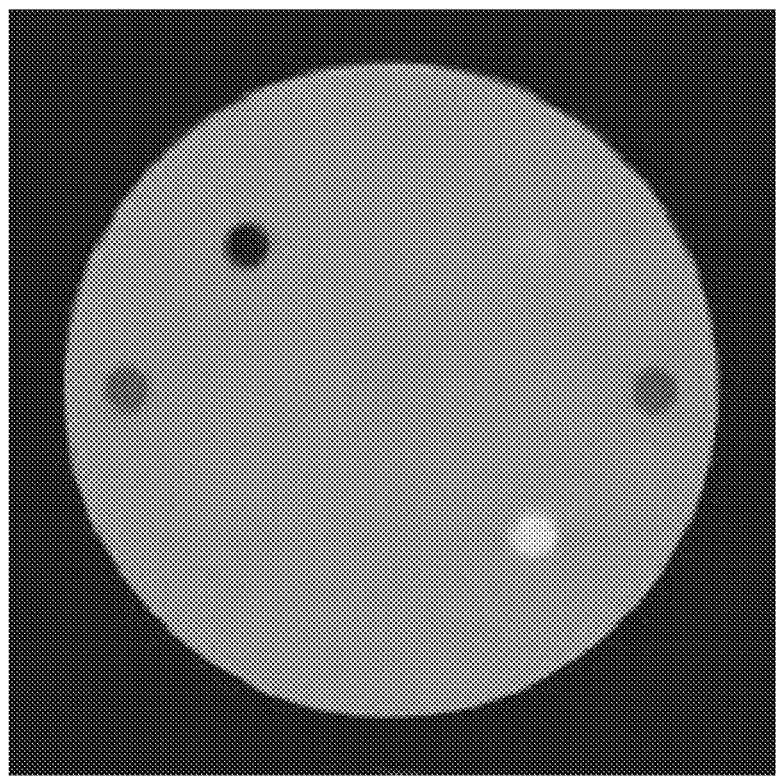
FIG. 30 shows an example proton CT image obtained using a selected reconstruction scheme applied to experimental proton data.

FIG. 30 shows an example proton CT image obtained using the TVS-DROP reconstruction scheme applied to experimental proton data. The image corresponds to a 2 mm slice reconstruction of a spherical phantom made of polystyrene (relative stopping power of about 1.035) with inserts of air (upper left), acyrlic (upper right, relative stopping power of about 1.2) and bone equivalent plastic (lower right, relative stopping power of about 1.7). One can see that different stopping power materials can be distinguished distinctly.

As described herein, a superiorization scheme can be applied to pCT reconstructions to suit an imaging task at hand. In some implementations, the superiorization methodology applied to pCT or other iterative image reconstruction methods can be facilitated by perturbing the calculated image estimates between the iterative steps of a feasibility seeking projection method. By choosing the method of perturbation appropriately, significant beneficial alterations to the sequence of reconstructed images can be achieved.

As described herein, example superiorization schemes such as TVS1-DROP and TVS2-DROP, based on a reduction of total variation, can yield improved image quality relative to the DROP methodology. More particularly, the additional perturbation steps utilized in TVS2-DROP can yield a greater reduction of image noise and superior density resolution.

In some implementations, computation time associated with one or more features of the total variation superiorization methodology can be considered in view of benefits provided. For example, calculation of the TV merit function (e.g., Equation 9) and the perturbation vector $v^k$ can increase image reconstruction time when the dimension of the image is relatively large. In another example, reconstruction time can increase significantly with the calculation of the feasibility proximity function (e.g., Equation 8). Thus, in some implementations, TVS schemes can be performed in a reduced time (e.g., about half the time) with the omission of the feasibility proximity function. In some implementations such as the TVS2-DROP scheme, the omission further reduction in the image noise can occur. In some implementations such as the TVS1-DROP scheme, the omission can have substantially no detrimental effect on other performance parameters.

It is also noted that in some implementations, improvement in spatial resolution can be achieved with both TVS facilitated reconstruction schemes. While the example TVS1-DROP* scheme as described herein displays a marginally superior spatial resolution than the TVS2-DROP* scheme, the latter still results in superior spatial resolution relative to an image reconstructed with the DROP reconstruction despite its better noise reduction. It has been noted that previous attempts to improve density resolution by "smoothing" the reconstructed image, in general, resulted in a degradation of spatial resolution. This is not the case in the example schemed TVS1-DROP and TVS2-DROP, where the spatial resolution was maintained or improved.

As described herein, one or more features of the present disclosure can facilitate effective and relatively fast reconstruction of proton CT data so as to obtain useful results such as images. Such advantageous features can also be utilized to reduce the amount of radiation dose needed to obtain such useful results. For example, and referring to FIGS. 5 and 6, protons used for CT can be configured such that on average, Bragg peak occurs at a location downstream of an object being imaged. Accordingly, the object is spared from receiving a substantial portion of the protons' radiation dose.

The amount of dose (without the Bragg peak energy loss) that an object can be expected to receive can be roughly estimated as follows. Suppose that an object being imaged is divided into voxels, with each voxel being a 1 mm$^3$ cube, and to obtain a slice image, proton projections are obtained at 180 orientations (similar to the example simulation of FIG. 26). For the purpose of the rough estimate, also assume that the object is a typical head sized object that can be represented by water, such that energy loss is about 100 MeV for 250 MeV protons. Then, a dose per proton for such a slice can be estimated to be about 0.5 nGy.

The dimension of a vector representative of the foregoing slice can be estimated as being $180^2=3.6\times10^4$, assuming the example voxel size of 1 mm$^3$ cube. Suppose that each voxel is crossed by at least one proton. Then, the number of protons that can be expected to be needed to cover such a slice can be estimated to be on the order of magnitude of the vector dimension. Accordingly, a dose that a given slice can be expected to receive can be estimated as $(3.6\times10^4)$ protons$\times 0.5$ nGy/proton=$1.8\times10^4$ nGy, or about 20 μGy (or about 20 μSv since protons in the 250 MeV range are generally low-LET radiation). Such a dosage is relatively low, and in some situations, can even be considered to be ultra-low.

Additional details concerning one or more features of the present disclosure can be found in an article by S. N. Penfold, R. W. Schulte, Y. Censor, A. B. Rosenfeld, "Total variation superiorization schemes in proton computed tomography image reconstruction," Med. Phys. 37 (11), November 2010, which is hereby incorporated herein by reference in its entirety.

The various example processes and algorithms described herein may be implemented as electronic hardware, computer software, or combinations of both. The hardware and data processing apparatus used to implement the various processes and algorithms may be implemented or performed with a general purpose single- or multi-chip processor, a digital signal processor (DSP), a general purpose graphical processing unit (GPGPU), an application specific integrated circuit (ASIC), a field programmable gate array (FPGA) or other programmable logic device, discrete gate or transistor logic, discrete hardware components, or any combination thereof designed to perform the functions described herein. A processor may be a microprocessor, or, any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. In some implementations, particular steps and methods may be performed by circuitry that is specific to a given function.

Various functions described herein may be implemented in hardware, digital electronic circuitry, computer software, firmware, or in any combination thereof. Implementations of the reconstruction schemes described herein can be implemented as one or more computer programs (e.g., one or more modules of computer program instructions, encoded on a computer storage media for execution by, or to control the operation of, data processing apparatus).

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media can include both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

The terms "approximately," "about," and "substantially" as used herein represent an amount close to the stated amount that still performs the desired function or achieves the desired result. For example, the terms "approximately", "about", and "substantially" may refer to an amount that is within less than 10% of, within less than 5% of, within less than 1% of, within less than 0.1% of, and within less than 0.01% of the stated amount. The term "at least a portion of" as used herein represents an amount of a whole that comprises an amount of the whole that may include the whole. For example, the term "a portion of" may refer to an amount that is greater than 0.01% of, greater than 0.1% of, greater than 1% of, greater than 10% of, greater than 20% of, greater than 30% of, greater than 40% of, greater than 50% of, greater than 60%, greater than 70% of, greater than 80% of, greater than 90% of, greater than 95% of, greater than 99% of, and 100% of the whole.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times.

The teachings of the invention provided herein can be applied to other systems, not necessarily the system described above. The elements and acts of the various embodiments described above can be combined to provide further embodiments.

While certain embodiments of the inventions have been described, these embodiments have been presented by way of example only, and are not intended to limit the scope of the disclosure. Indeed, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method for performing computed tomography, the method comprising:
    delivering a particle beam to an object, the particle beam comprising a plurality of positive ions;
    measuring, with one or more particle detectors, a trajectory and an interaction quantity for individual positive ions in the particle beam that pass through the object;
    generating a system of linear equations representing the passage of the individual positive ions through the object, the system of linear equations arranged in the form of $Ax=b$, where x is a discrete object vector representing an object parameter distribution, b is a vector that represents the measured interaction quantities of the individual positive ions resulting from interactions along their respective paths in the object, and A is a matrix comprising individual elements that correspond to an estimated intersection length of an individual positive ion in a corresponding voxel based at least in part on an estimated path through the object, wherein the system of linear equations has a plurality of solutions forming a set of feasible solutions;
    determining, using one or more computer processors, a solution for the system of linear equations using a superiorization procedure comprising performing N superiorization cycles, each superiorization cycle comprising:
        perturbing the discrete object vector x using a perturbation corresponding to a gradient of a merit function;
        projecting the perturbed discrete object vector x using a perturbation resilient projection algorithm; and
        replacing the discrete object vector x with the projected, perturbed discrete object vector x; and
    generating a computed tomography image of the object based at least in part on the determined solution that comprises the discrete object vector x after the superiorization procedure has been performed,
    wherein the number of cycles, N, is greater than or equal to 2.

2. The method of claim 1, wherein the determined solution has a superior characteristic with respect to the merit function than a solution determined without performing the step of perturbing the discrete object vector x.

3. The method of claim 1, wherein the method does not calculate proximity to the set of feasible solutions for the projected, perturbed discrete object vector x.

4. The method of claim 3, wherein the method does not calculate proximity to the set of feasible solutions for the discrete object vector x.

5. The method of claim 1 further comprising forming M blocks from the measured data.

6. The method of claim 1, wherein the perturbation resilient projection algorithm comprises a block-iterative projection algorithm.

7. The method of claim 1, wherein the interaction quantity comprises an energy loss of the positive ion resulting from its passage through the object.

8. The method of claim 1, wherein the object parameter distribution comprises a distribution of an electron density-based quantity.

9. The method of claim 8, wherein the electron density-based quantity comprises relative proton stopping power with respect to water.

10. The method of claim 1 further comprising calculating an estimate of an initial solution using a filtered backprojection reconstruction, the estimated initial solution being used as the discrete object vector x in the first cycle of the superiorization procedure.

11. The method of claim 1, wherein the positive ions comprise protons.

12. The method of claim 1, wherein the positive ions comprise carbon ions.

13. A method for performing computed tomography, the method comprising:
 delivering a particle beam to an object, the particle beam comprising a plurality of positive ions;
 measuring, with one or more particle detectors, a trajectory and an interaction quantity for individual positive ions in the particle beam that pass through the object;
 generating a system of linear equations representing the passage of the individual positive ions through the object, the system of linear equations arranged in the form of $Ax=b$, where x is a discrete object vector representing an object parameter distribution, b is a vector that represents the measured interaction quantities of the individual positive ions resulting from interactions along their respective paths in the object, and A is a matrix comprising individual elements that correspond to an estimated intersection length of an individual positive ion in a corresponding voxel based at least in part on an estimated path through the object, wherein the system of linear equations has a plurality of solutions forming a set of feasible solutions;
 determining, using one or more computer processors, a solution for the system of linear equations using a superiorization procedure comprising performing N superiorization cycles, each superiorization cycle comprising:
  perturbing the discrete object vector x using a perturbation corresponding to a gradient of a merit function, wherein the merit function comprises a total variation of the object parameter distribution;
  projecting the perturbed discrete object vector x using a perturbation resilient projection algorithm; and
  replacing the discrete object vector x with the projected, perturbed discrete object vector x; and
 generating a computed tomography image of the object based at least in part on the determined solution that comprises the discrete object vector x after the superiorization procedure has been performed,
 wherein the number of cycles, N, is greater than or equal to 2.

14. A method for performing computed tomography, the method comprising:
 delivering a particle beam to an object, the particle beam comprising a plurality of positive ions;
 measuring, with one or more particle detectors, a trajectory and an interaction quantity for individual positive ions in the particle beam that pass through the object;
 generating a system of linear equations representing the passage of the individual positive ions through the object, the system of linear equations arranged in the form of $Ax=b$, where x is a discrete object vector representing an object parameter distribution, b is a vector that represents the measured interaction quantities of the individual positive ions resulting from interactions along their respective paths in the object, and A is a matrix comprising individual elements that correspond to an estimated intersection length of an individual positive ion in a corresponding voxel based at least in part on an estimated path through the object, wherein the system of linear equations has a plurality of solutions forming a set of feasible solutions;
 determining, using one or more computer processors, a solution for the system of linear equations using a superiorization procedure comprising performing N superiorization cycles, each superiorization cycle comprising:
  perturbing the discrete object vector x using a perturbation corresponding to a gradient of a merit function;
  projecting the perturbed discrete object vector x using a perturbation resilient projection algorithm; and
  replacing the discrete object vector x with the projected, perturbed discrete object vector x; and
 generating a computed tomography image of the object based at least in part on the determined solution that comprises the discrete object vector x after the superiorization procedure has been performed,
 wherein the number of cycles, N, is less than or equal to 10.

15. The method of claim 14, wherein the number of cycles, N, is less than or equal to 6.

16. A method for performing computed tomography, the method comprising:
 delivering a particle beam to an object, the particle beam comprising a plurality of positive ions;
 measuring, with one or more particle detectors, a trajectory and an interaction quantity for individual positive ions in the particle beam that pass through the object;
 generating a system of linear equations representing the passage of the individual positive ions through the object, the system of linear equations arranged in the form of $Ax=b$, where x is a discrete object vector representing an object parameter distribution, b is a vector that represents the measured interaction quantities of the individual positive ions resulting from interactions along their respective paths in the object, and A is a matrix comprising individual elements that correspond to an estimated intersection length of an individual positive ion in a corresponding voxel based at least in part on an estimated path through the object, wherein the system of linear equations has a plurality of solutions forming a set of feasible solutions;

forming M blocks from the measured data;

determining, using one or more computer processors, a solution for the system of linear equations using a superiorization procedure comprising performing N superiorization cycles, each superiorization cycle comprising:

perturbing the discrete object vector x using a perturbation corresponding to a gradient of a merit function;

projecting the perturbed discrete object vector x using a perturbation resilient projection algorithm, wherein projecting the perturbed discrete object vector x comprises projecting the perturbed discrete object vector x sequentially onto each of the M blocks prior to proceeding to the next cycle; and replacing the discrete object vector x with the projected, perturbed discrete object vector x; and generating a computed tomography image of the object based at least in part on the determined solution that comprises the discrete object vector x after the superiorization procedure has been performed, wherein the number of cycles, N, is greater than or equal to 2.

17. A method for performing computed tomography, the method comprising:

delivering a particle beam to an object, the particle beam comprising a plurality of positive ions;

measuring, with one or more particle detectors, a trajectory and an interaction quantity for individual positive ions in the particle beam that pass through the object;

generating a system of linear equations representing the passage of the individual positive ions through the object, the system of linear equations arranged in the form of $Ax=b$, where x is a discrete object vector representing an object parameter distribution, b is a vector that represents the measured interaction quantities of the individual positive ions resulting from interactions along their respective paths in the object, and A is a matrix comprising individual elements that correspond to an estimated intersection length of an individual positive ion in a corresponding voxel based at least in part on an estimated path through the object, wherein the system of linear equations has a plurality of solutions forming a set of feasible solutions;

forming M blocks from the measured data;

determining, using one or more computer processors, a solution for the system of linear equations using a superiorization procedure comprising performing N superiorization cycles, each superiorization cycle comprising:

perturbing the discrete object vector x using a perturbation corresponding to a gradient of a merit function;

projecting the perturbed discrete object vector x using a perturbation resilient projection algorithm; and replacing the discrete object vector x with the projected, perturbed discrete object vector x; and generating a computed tomography image of the object based at least in part on the determined solution that comprises the discrete object vector x after the superiorization procedure has been performed, wherein the number of cycles, N, is greater than or equal to 2; and wherein the superiorization procedure comprises for each of the M blocks, repeating the superiorization cycle N times for each selected block.

18. A computed tomography system comprising:

a particle beam delivery system configured to deliver a particle beam to an object, the particle beam comprising a plurality of positive ions;

one or more particle detectors configured to measure a trajectory and an interaction quantity for individual positive ions that pass through the object;

computer hardware and a physical storage device, the physical storage device comprising instructions executable by the computer hardware, the instructions comprising:

first instructions to generate a system of linear equations representing the passage of the individual positive ions through the object, the system of linear equations arranged in the form of $Ax=b$, where x is a discrete object vector representing an object parameter distribution, b is a vector that represents the measured interaction quantities of the individual positive ions resulting from interactions along their respective paths in the object, and A is a matrix comprising individual elements that correspond to an estimated intersection length of an individual positive ion in a corresponding voxel based at least in part on an estimated path through the object, wherein the system of linear equations has a plurality of solutions forming a set of feasible solutions;

second instructions to determine a solution for the system of linear equations using a superiorization procedure comprising performing N superiorization cycles, each superiorization cycle comprising:

perturbing the discrete object vector x using a perturbation corresponding to a gradient of a merit function;

projecting the perturbed discrete object vector x using a perturbation resilient projection algorithm; and replacing the discrete object vector x with the projected, perturbed discrete object vector x; and third instructions to generate a computed tomography image of the object based at least in part on the determined solution that comprises the discrete object vector x after the superiorization procedure has been performed, wherein the number of cycles, N, is greater than or equal to 2.

19. The system of claim 18, wherein the one or more particle detectors comprise:

upstream tracking detectors configured to measure data indicative of a spatial vector and location of a positive ion prior to passage through the object;

downstream tracking detectors configured to measure data indicative of a spatial vector and location of a positive ion after passage through the object; and an energy detector configured to detect an energy of a positive ion after passage through the object.

20. The system of claim 19, wherein the one or more particle detectors are configured to rotate about an axis of the object.

* * * * *